United States Patent [19]

Ono et al.

[11] Patent Number: 4,656,288

[45] Date of Patent: Apr. 7, 1987

[54] ANTIBIOTICS, THEIR PRODUCTION AND USE

[75] Inventors: Hideo Ono, Kobe; Yukimasa Nozaki, Ikeda; Setsuo Harada, Kawanishi, all of Japan

[73] Assignee: Takeda Chemical Industries, Ltd., Osaka, Japan

[21] Appl. No.: 714,084

[22] Filed: Mar. 20, 1985

[30] Foreign Application Priority Data

| Mar. 29, 1984 | [JP] | Japan | PCT/JP84/00150 |
| Apr. 27, 1984 | [JP] | Japan | PCT/JP84/00222 |
| Nov. 29, 1984 | [JP] | Japan | PCT/JP84/00568 |
| Feb. 28, 1985 | [JP] | Japan | PCT/JP85/00095 |

[51] Int. Cl.$^4$ .................... C07D 261/02; A61K 31/42
[52] U.S. Cl. .................... 548/244; 435/68; 435/118; 514/380
[58] Field of Search ............... 548/244; 514/380

[56] References Cited

U.S. PATENT DOCUMENTS 4,275,214  6/1981  Kelly et al. .................... 548/244

FOREIGN PATENT DOCUMENTS 787741  12/1957  United Kingdom .................... 548/244

OTHER PUBLICATIONS

Patel, G. B., "... Properties of *Methanothrix concilli* sp. nov. ...," Can. J. Microbiol., 30, (1984), pp. 1383–1396.
Akira Tsuji et al.; Heterocycles 8, 153(1977).
Jun'ichi Shoji et al.; Journal of Antibiotics 37, 1198 (1984).

*Primary Examiner*—Glenna M. Hendricks
*Attorney, Agent, or Firm*—Wenderoth, Lind & Ponack

[57] ABSTRACT

Antibiotic TAN-558 produced by a microorganism of the genus Empedobacter or genus Lysobacter, its p-nitrobenzyl- or benzhydryl ester derivative, or their N-deacetylated derivatives or salts thereof possess antimicrobial activities against Gram-positive and Gram-negative bacteria, and can be used as a therapeutic agent for bacterial infections in mammals, fowls, etc.

4 Claims, 12 Drawing Figures

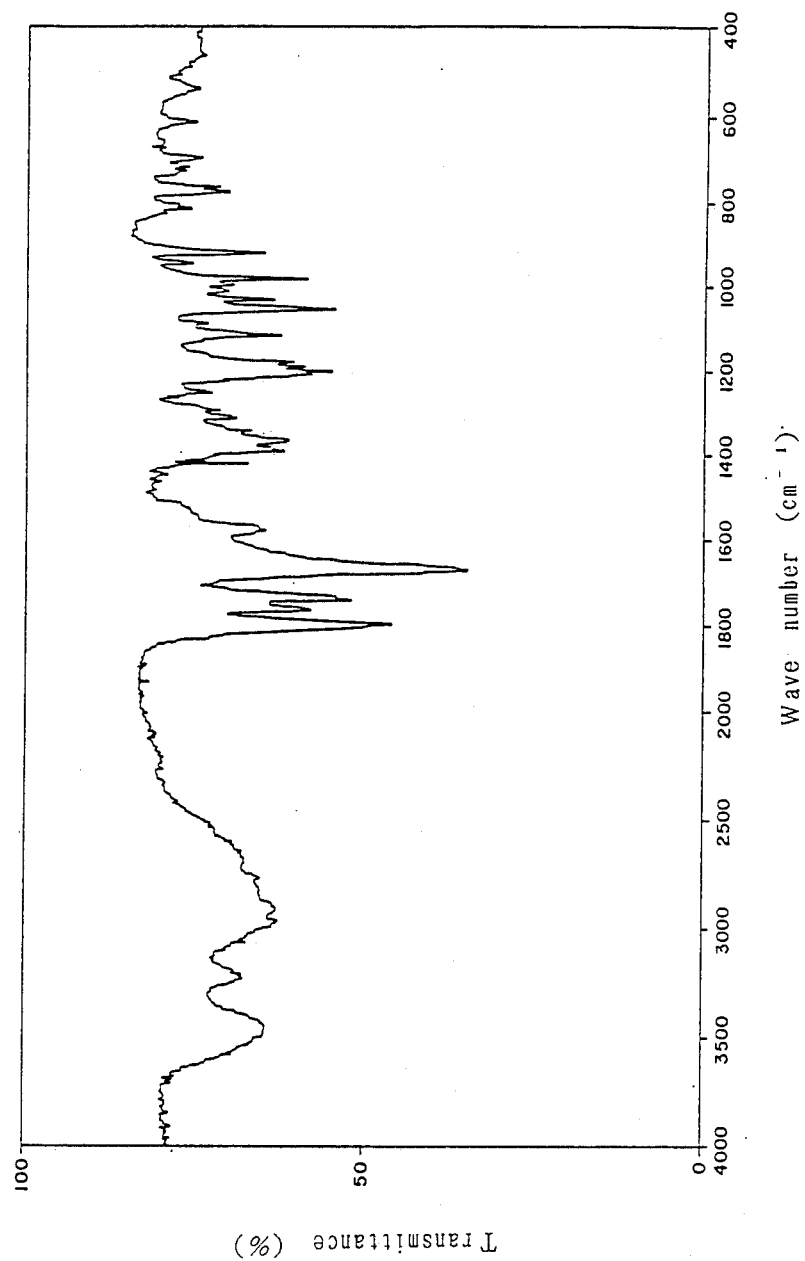

ANTIBIOTICS, THEIR PRODUCTION AND USE

The present invention relates to a novel antibiotic which is useful as an antimicrobial agent, etc., to a process for producing the same, and its use.

As the antibiotic exhibiting inhibitory activity of cell wall synthesis which is produced by bacteria, heretofore, there have been known sulfazecin and isosulfazecin (Nature, 289, 590–591, 1981), and subsequently, there have been also discovered SQ 26180, 26700, 26823, 26875, 26970, 26812, etc. (Nature, 291, 489–491, 1981). These are known as the antibiotic which exhibits principally antimicrobial activity against Gram-negative bacteria. In addition, the reports were recently presented on SQ 28332, 28502, 28503, etc. (J. Antibiotics, 36, 1245–1251: 1252–1257, 1983).

The present inventors, with a specific view to the search for novel antibiotics, isolated a large number of microorganisms from soil, and performed screenings for identifying the antibiotics which the microorganisms produce. As a result, it was found that a certain microorganism is able to produce a novel antibiotic, that the said microorganism is a novel species of the genus Empedobacter or the genus Lysobacter, and that cultivation of the said microorganism in a suitable culture medium results in accumulation in the culture medium of the antibiotic which exhibits antimicrobial activity against Gram-positive and Gram-negative bacteria, and this antibiotic was isolated; its physico-chemical and biological characteristics led to the confirmation that the said antibiotic is a novel antibiotic, and it has been decided that this is referred to as "Antibiotic TAN-588".

The present inventors found that the above Antibiotic TAN-588 has N-acetyl and carboxyl groups in the molecule and that the said acetyl group can be removed.

Furthermore, the present inventors found that a microorganism belonging to the genus Empedobacter or the genus Lysobacter can produce a N-deacetylated derivative of the Antibiotic TAN-588, and that when a microorganism belonging to the genus Acinetobacter and a microorganism belonging to the genus Empedobacter or the genus Lysobacter are cultivated in the culture medium, a N-deacetylated derivative of the Antibiotic TAN-588 is produced in a large amount than only the microorganism belonging to the genus Empedobacter or the genus Lysobacter is employed.

These findings were followed by further research, which has culminated into the present invention.

The present invention is directed to: (1) Antibiotic TAN-588, its para-nitrobenzyl or benzhydryl derivative, or their N-deacetylated derivatives or salts of these compounds; (2) A method for producing Antibiotic TAN-588 and/or its N-deacetylated derivative or their salts, which comprises cultivating a microorganism which belongs to the genus Empedobacter or the genus Lysobacter and is capable of producing Antibiotic TAN-588 and/or its N-deacetylated derivative in a culture medium to have Antibiotic TAN-588 and/or its N-deacetylated derivative elaborated and accumulated in the culture broth and recovering the said antibiotic; (3) A method for producing the N-deacetyl Antibiotic TAN-588 or its salts, which comprises deacetylating Antibiotic TAN-588 or its salt; (4) A process for producing the benzhydryl ester derivative of the N-deacetyl Antibiotic TAN-588, which comprises reacting Antibiotic TAN-588 or its salts with a compound capable of allowing the introduction of a benzhydryl group to convert into the benzhydryl ester derivative of Antibiotic TAN-588, and subjecting the benzhydryl ester derivative to deacetylation; and (5) A method for producing N-deacetyl Antibiotic TAN-588, which comprises carrying out the mixed cultivation of a microorganism which belongs to the genus Empedobacter or the genus Lysobacter and is capable of producing Antibiotic TAN-588 and/or its N-deacetylated derivative and of a microorganism which belongs to the genus Acinetobacter and is capable of having said microorganism of the genus Empedobacter or Lysobacter produce N-deacetyl Antibiotic TAN-588 in a culture medium to have N-deacetyl Antibiotic TAN-588 elaborated and accumulated in the culture broth and recovering the said antibiotic.

In this specification, Antibiotic TAN-588 is in some instances referred to as merely "TAN-588".

The microorganism capable of producing Antibiotic TAN-588 and/or its N-deacetylated derivative, which is used in the present invention, may be any type of microorganisms, only when they possess the capacity to produce Antibiotic TAN-588. The examples include, for example, *Empedobacter lactamgenus* which is a novel species of microorganism. As its specific example, there may be mentioned *Empedobacter lactamgenus* YK-258 strain (hereinafter referred to, in some instances, briefly as "YK-258 strain") which was isolated from a soil sample collected at Masuda city, Shimane Prefecture, Japan.

The microbiological characteristics of YK-258 strain are as described in the following.

(a) Morphological characteristics

The observation after incubation of the strain on a nutrient agar slant at 24° C. for 5 days indicates that the cells are in the form of elongated rod having a diameter of 0.4 to 0.6 $\mu$m and a length of 2.0 to 3.0 $\mu$m and are occasionally shaped like filament having a length of 12 to 30 $\mu$m, but show no flagellum, with no cell motility found; and that the cells form no spore, are Gram-negative and not acid-fast.

(b) Growths on various culture media

Cultivation was conducted at 24° C., and observations were made over the period of 1 to 14 days.

(1) Nutrient agar plate culture:

The formed colonies are translucent, pale yellowish, circular-shaped, with papillate surface and entire margin; no diffusible pigment produced.

(2) Nutrient agar slant culture:

The colonies show good effuse growth and develop yellowish to amber color.

(3) Nutrient broth culture:

The culture grows turbid and produces a precipitate, with pellicle formed.

(4) Nutrient gelatin stab culture:

Growth mainly on the upper part, with crater-form liquefaction. Liquefaction activity is relatively weak.

(5) Litmus milk:

No activity for reduction of Litmus, peptonization and coagulation observed.

(c) Physiological characteristics (1) Reduction of nitrates: —
(2) Denitrification reaction: —
(3) MR (Methyl red) test: —
(4) VP (Voges-Proskauer) test: —
(5) Production of indole: —

(6) Production of hydrogen sulfide (TSI agar and lead acetate paper): —
(7) Hydrolysis of starch: —
(8) Utilization of citrate (on Koser's, Christensen's and Simmons' culture media): +
(9) Utilization of inorganic nitrogen sources:
  (i) Potassium nitrate: —
  (ii) Ammonium sulfate: —
(10) Production of pigments (on King A and B and mannit-yeast extract agar culture media): No diffusible pigment production observed.
(11) Urease: —
(12) Oxidase: +
(13) Catalase: —
(14) Ranges for the growth:
  (i) pH: The optimal pH ranges from 5.8 to 6.6, though the microorganism grows at pH of 5.4 to 8.5. Culture medium: 0.1% of glucose, 0.01% of yeast extract, 0.1% of ammonium sulfate, 0.1% of sodium chloride, 0.05% of magnesium sulfate (heptahydrate) and 0.1 M of phosphate buffer (sterilized separately).
  (ii) Temperature: The optimum temperature is 24° to 31° C., though the microorganism grows at 20° to 32° C. Culture medium: Nutrient broth culture medium.
(15) Oxygen demand: Aerobic
(16) O-F (Oxidative-Fermentative) test (Hugh-Leifson method): Not reactive
(17) Acid and gas production from sugars and their utilization:

|  | Acid (Aqueous peptone) | Gas (Aqueous peptone) | Utilization (Davis culture medium) |
|---|---|---|---|
| L-Arabinose | — | — | — |
| D-Xylose | ± | — | — |
| D-Glucose | — | — | + |
| D-Mannose | — | — | + |
| D-Fructose | — | — | + |
| D-Galactose | — | — | — |
| Maltose | — | — | + |
| Sucrose | — | — | — |
| Lactose | — | — | — |
| Trehalose | — | — | + |
| D-Sorbitol | — | — | — |
| D-Mannitol | — | — | — |
| Inositol | — | — | — |
| Glycerol | — | — | — |
| Starch | — | — | + |

(18) The mol% G+C of the DNA: 74.4±1.5 (Tm method)
(19) Capacities to decompose polysaccharides:
Carboxymethylcellulose: +
Colloidal chitin: +
Sodium alginate:
(20) Tolerance to actinomycin: Resistant The strain YK-258 having the above-described microbiological characteristics was compared with the strains as described in "Bergey's Mannual of Determinative Bacteriology, 8th edition" and "International Journal of Systematic Bacteriology, 30, 225–420 (1980) and 32, 146–149 (1982), and on the basis of the observations that the strain is a yellowish Gram-negative, with no cell motility, being aerobic, lacks the capacity to produce acid and gas from sugars and shows a high GC content of DNA, it is considered appropriate that the strain belongs to the genus Flavobacterium. However, it has been pointed out from the standpoint of bacterial taxonomy that the Flavobacterium strains heretofore described are mingled with foreign, different species of microorganisms, and the definition of the genus Flavobacterium was recently corrected in "International Journal of Systematic Bacteriology", 29, 416–426 (1979). According to the said literature reference and "Annual Review of Microbiology", 37, 233–252 (1983), it is regarded as more reasonable that the strain YK-258 belongs to rather the genus Empedobacter than the genus Flavobacterium. Nevertheless, among these is not found the description of a species that exhibits the GC content of the DNA in excess of 70%. The above finding suggests that the strain YK-258 was identified as a strain belonging to the novel species of microorganism and that the said novel species of microorganism was named *Empedobacter lactamgenus*.

The above strain *Empedobacter lactamgenus* YK-258 has been deposited at the Institute for Fermentation, Osaka (IFO: 17-85, Juso-honmachi 2-chome, Yodogawa-ku, Osaka, Japan) as the accession number IFO 14322 as from the Feb. 20th, 1984. The said microorganism has also been deposited at the Fermentation Research Institute, Agency of Industrial Science and Technology, Ministry of International Trade and Industry, Japan (FRI: 1-3, Yatabe-cho higashi 1-chome, Tsukuba-gun, Ibaragi Prefecture, Japan) as the accession number FERM P-7558 as from the Mar. 26th 1984, and the deposit has been converted to a deposit under the Budapest Treaty and has been stored at the FRI under the accession number of FERM BP-699.

Examples of the microorganism of the genus Lysobacter capable of producing Antibiotic TAN-588 and/or its N-deacetylated derivative, which is usable in the present invention, include, for example, *Lysobacter albus*, a new species of microorganism. As its specific example, there may be mentioned the strain *Lysobacter albus* sp. nov. YK-422 (hereinafter referred to in some instances briefly as "YK-422"), which the present inventors isolated from the soil collected at Kanzaki-gun, Shiga Prefecture, Japan.

The microbiological characteristics of the strain YK-422 are as described in the following:
(a) Morphological characteristics The observation after incubation of the strain on a nutrient agar slant at 24° C. for 2 days indicates that the cells are in the form of elongated rod having a diameter of 0.4 to 0.7 μm and a length of 2.0 to 4.4 μm and are occasionally shaped like filament having a length of 20 to 30 μm, but show no flagellum, with no cell motility found; and that the cells form no spore nor microcyst, are negative to Gram-staining and not acid-fast.

(b) Growths on various culture media

Cultivation was conducted at 24° C., and observations were made over the periods of 1 to 14 days.
(1) Nutrient agar plate culture:
The formed colonies are translucent, white, circular-shaped, with convex surface and entire margin, and show mucoidal surface growth; no diffusible pigment produced.
(2) Nutrient agar slant culture:
The colonies show good filamentous growth and develop white color.
(3) Nutrient broth culture:
The culture grows slightly turbid and produces a small amount of precipitate, with weak fairy ring formed.
(4) Nutrient gelatin stab culture:

Growth is observed on the upper part, with stratiform liquefaction. Liquefaction activity is relatively strong.

(5) Litmus milk:

Reduction of Litmus and peptonization are observed, with no coagulation found.

(6) Dried yeast plate culture: Cleared zone is formed in the peripheries of colonies formed, with motility through gliding being shown.

(c) Physiological characteristics (1) Reduction of nitrates: —

(2) Denitrification reaction: —

(3) MR (Methyl red) test: —

(4) VP (Voges-Proskauer) test: —

(5) Production of indole: —

(6) Production of hydrogen sulfide (TSI agar and lead acetate paper): —

(7) Hydrolysis of starch: —

(8) Utilization of citrate (on Christensen's and Simmons' culture media): +

(9) Utilization of inorganic nitrogen sources:

(i) Potassium nitrate: —

(ii) Ammonium sulfate: —

(10) Production of pigments (on King A and B and mannit-yeast extract agar culture media): No diffusible pigment production observed.

(11) Urease: —

(12) Oxidase: +(13) Catalase: —

(14) Ranges for the growth:

(i) pH: The optimal pH ranges from 6.3 to 7.9, though the microorganism grows at a pH of 4.6 to 8.2. Culture medium: 0.1% of glucose, 0.01% of yeast extract, 0.1% of ammonium sulfate, 0.1% of sodium chloride and 0.05% of magnesium sulfate (heptahydrate), with the pH adjusted with sodium hydroxide or sulfuric acid.

(ii) Temperature: The optimum temperature is 21° to 28° C., though the microorganism grows at 14° to 32° C. Culture medium: Nutrient broth medium.

(15) Oxygen demand: Aerobic

(16) O-F (Oxidative-Fermentative) test (Hugh.Leison method): Not reactive.

(17) Acid and gas production from sugars and their utilization:

| | Acid (Aqueous peptone) | Gas (Aqueous peptone) | Utilization (Davis culture medium) |
|---|---|---|---|
| L-Arabinose | — | — | ± |
| D-Xylose | — | — | + |
| D-Glucose | — | — | + |
| D-Mannose | — | — | + |
| D-Fructose | — | — | + |
| D-Galactose | — | — | + |
| Maltose | — | — | + |
| Sucrose | — | — | + |
| Lactose | — | — | + |
| Trehalose | — | — | + |
| D-Sorbitol | — | — | — |
| D-Mannitol | — | — | + |
| Inositol | — | — | — |
| Glycerol | — | — | ± |
| Starch | — | — | + |

(18) The mol% G+C of the DNA: 70.2±1.5 (Tm method).

(19) Capacities to decompose polysaccharides:
Carboxymethylcellulose: +
Colloidal chitin: +
Sodium alginate: ±

The strain YK-422 showing the above-described microbiological characteristics was compared with the strains as described in "Bergey's Mannual of Determinative Bacteriology, 8th edition" and "International Journal of Systematic Bacteriology", 30, 225–420 (1980) and 32, 146–149 (1982) as well as validation lists in the relevant literature, and on the basis of the observations that the microorganism is a Gram-negative bacterium exhibiting mucoidal growth, being observed to occur partially in the form of a filamentous organism, shows motility through gliding, possesses the ability to decompose colloidal chitin and dried yeast, forms no microcyst and shows a high GC content in DNA, it is considered appropriate that the strain belongs to the genus Lysobacter. However, the strain differed from the heretofore described species of the genus Lysobacter ("International Journal of Systematic Bacteriology", 28, 367–393 (1978)) in that it is not reactive in O-F test, forms colonies showing no distinctive color tone and possesses no capability to assimilate and digest the inorganic nitrogen source. The above findings suggest that the YK-422 strain was identified as a strain belonging to the novel species of microorganism and that the said novel species of microorganism was named *Lysobacter albus* sp. nov.

The above strain Lysobacter albus sp. nov. YK-422 has been deposited at the IFO as the accession number IFO 14384 as from the Oct. 5th 1984. The said strain has also deposited at the FRI as the accession number FERM P-7938 as from Nov. 14th 1984, and the deposit has been converted to a deposit under the Budapest Treaty and has been stored at the FRI under the accession number of FERM BP-698.

In the present mixed cultivation, a microorganism belonging to the genus Acinetobacter and capable of having TAN-588 and/or its N-deacetylated derivative-producing microorganism of the genus Empedobacter or Lysobacter produce N-deacetylated derivative of TAN-588 in a large amount.

Said large amount means that the amount of N-deacetyl Antibiotic TAN-588 in the mixed cultivation is much more than the amount of N-deacetyl Antibiotic TAN-588 in the cultivation employing only the microorganism of the genus Empedobacter or Lysobacter.

As the example of the microorganism of the genus Acinetobacter, there may be mentioned the strain Acinetobacter sp. YK-504 (hereinafter referred to in some instances briefly as "YK-504".), which the present inventors isolated from the sweet water collected at Yodogawa-ku, Osaka City, Osaka Prefecture, Japan.

The microbiological characteristics of the strain YK-504 are as described in the following:

(a) Morphological characteristics

The observation after incubation of the strain on a nutrient agar slant at 24° C. for 5 days indicates that the cells are in the form of short rod or spherical having a diameter of 0.8 to 1.5 μm and a length of 1.1 to 2.1 μm and occures occasionally in pairs and filament, but show no flagellum, with no cell motility found; and that the cells form no spore nor microcyst, are negative to Gram-staining and not acid-fast.

(b) Growths on various culture media

Cultivation was conducted at 24° C., and observations were made over the periods of 4 to 14 days.

(1) Nutrient agar plate culture:

The formed colonies are small, circular-shaped, with convex surface and entire margin, no diffusible pigment produced.

(2) Nutrient agar slant culture:

The colonies show moderate filamentous growth and are colorless and glossy.

(3) Nutrient broth culture:

The culture grows turbid and produces a precipitate, with no ring formed.

(4) Nutrient gelatin stab culture:

Weak growth is observed on the upper part. Liquefaction activity is negative.

(5) Litmus milk:

Reduction of Litmus and peptonization and coagulation are not observed.

(c) Physiological characteristics (1) Reduction of nitrates: —
(2) Denitrification reaction: —
(3) MR (Methyl red) test: —
(4) VP (Voges-Proskauer) test: —
(5) Production of indole: —
(6) Production of hydrogen sulfide (TSI agar and lead acetate paper): —
(7) Hydrolysis of starch: —
(8) Utilization of citrate (on Koser's, Christensen's and Simmons' culture media): —
(9) Utilization of inorganic nitrogen sources:
 (i) Potassium nitrate: —
 (ii) Ammonium sulfate: —
(10) Production of pigments (on King A and B and mannit-yeast extract agar culture media): No diffusible pigment production observed.
(11) Urease: —
(12) Oxidase: —
(13) Catalase: +
(14) Ranges for the growth:
 (i) pH: The optical pH range from 6 to 7.5, though the microorganism grows at a pH of 5 to 8. Culture medium: Nutrient broth with the pH adjusted with sodium hydroxide or sulfuric acid.
 (ii) Temperature: The optimum temperature is 15° to 22° C., though the microorganism grows at 7.5° to 39° C. Culture medium: Nutrient broth medium.
(15) Oxygen demand: Aerobic
(16) O-F (Oxidase-Fermentative) test (Hugh-Leison method): Not reactive.
(17) Acid and gas production from sugars and their utilization:

|  | Acid (Aqueous peptone) | Gas (Aqueous peptone) | Utilization (Davis culture medium) |
|---|---|---|---|
| L-Arabinose | — | — | — |
| D-Xylose | — | — | — |
| D-Glucose | — | — | — |
| D-Mannose | — | — | — |
| D-Fructose | — | — | — |
| D-Galactose | — | — | — |
| Maltose | — | — | — |
| Sucrose | — | — | — |
| Lactose | — | — | — |
| Trehalose | — | — | — |
| D-Sorbitol | — | — | — |
| D-Mannitol | — | — | — |
| Inositol | — | — | — |
| Glycerol | — | — | — |
| Starch | — | — | — |

(18) The mol% G+C of the DNA: 40.0±1.5 (Tm method).

(19) Capacities to decompose polysaccharides:
Carboxymethylcellulose: —
Colloidal chitin: —
Sodium alginate: —

The strain YK-504 showing the above-described microbiological characteristics was compared with the strains as described in "Bergey's Mannual of Determinative Bacteriology, 8th edition" and "International Journal of Systematic Bacteriology", 30, 225–420 (1980) and 32, 146–149 (1982) as well as validation lists in the relevant literature, and on the basis of the observations that the microorganism is Gram-negative short rod or spherical and is not motile, aerobic, does not form acid and gas from sugars. Oxidase test is negative. Catalase test is positive. The mol % G+C of the DNA is 40.0±1.5, the strain YK-504 is determined to belong to the genus Acinetobacter, and then designated as Acinetobacter sp. YK-504.

The above strain Acinetobacter sp. YK-504 has been deposited at the IFO as the accession number IFO 14420 as of Jan. 31, 1985, and at the FRI as the accession number FERM BP-709 as of Feb. 12, 1985.

The microorganism of the genus Empedobacter or the genus Lysobacter, which is usable in the present invention, generally shows properties and characteristics readily liable to undergo change or alteration, and is readily susceptible to mutation through aritificial mutation means using for example ultraviolet light, X-rays and chemical agents (e.g., nitrosoguanidine, ethylmethanesulfonic acid, etc.); any of its mutants can be used in the present invention, only if they are capable of producing TAN-588 and/or its N-deacetylated derivative that the present invention for its object.

The microorganism of the genus Acinetobacter, usable in the present invention, generally shows properties and characteristics readily liable to undergo change or alteration, and is readily susceptible to mutation through aritificial mutation means using for example ultraviolet light, X-rays and chemical agents (e.g., nitrosoguanidine, ethylmethanesulfonic acid, etc.); any of its mutants can be used in the present invention, only if they are capable of having Antibiotic TAN-588 and/or its N-deacetylated derivative-producing strain produce N-deacetyl Antibiotic TAN-588 in a large amount by the mixed cultivation of the present invention.

In cultivating the TAN-588 and/or its N-deacetylated derivative-producer, as the carbon source, there may be suitably used substances which the microorganism can assimilate and digest, such as glucose, fructose, maltose, soluble strach, dextrin, oils and fats (e.g., soybean oil, olive oil, etc.) and organic acids (e.g., citric acid, succinic acid, gluconic acid, etc.). As the nitrogen source, there can be utilized organic nitrogen compounds, such as soybean meal, cotton seed flour, corn gluten meal, dried yeast, yeast extract, meat extract, peptone and urea. As the inorganic salt, there may be used, solely or suitable combinations, inorganic salts which are normally necessary for the cultivation of microorganisms, such as sodium chloride, potassium chloride, calcium carbonate, magnesium sulfate, monopotassium phosphate and disodium phosphate.

In addition, heavy metal salts, such as ferrous sulfate and copper sulfate, vitamins, such as vitamin $B_1$, biotin, and the like are added, if necessary. Furthermore, antifoams and surfactant, such as silicone oil or polyalkylene glycol ether, may be added to the culture medium. Other organic and inorganic substances which help the microorganism to grow and promote the production of TAN-588 and/or its N-deacetylated derivative may be suitably added.

With reference to the cultural method, cultivation may be conducted by a procedure similar to the process for producing general antibiotics, and either solid culture or liquid culture may be adoptable. In the case of liquid culture, stationary culture, shake culture, submerged culture, aerobic culture, etc. may all be carried out, though aerobic submerged culture is particularly preferred. The incubation temperature is preferably in the range of about 15° C. to 32° C., whereby incubation is carried out with a pH of the culture medium ranging from about 5 to 8 for 8 to 168 hours, preferably 24 to 144 hours. It is preferable to carry out the cultivation about 18 to 48 hours so as to produce N-deacetyl TAN-588.

The mixed cultivation of the present invention is carried out by the manner similar to the manner of the production of TAN-588 and/or its N-deacetylated derivative by the cultivation of the microorganism of the genus Empedobacter or Lysobacter.

The detection of the N-deacetyl Antibiotic TAN-588 is carried out by TLC-bioautography method employing *Pseudomonas aeruginosa* C-141.

The present mixed cultivation employing a microorganism belonging to the genus Acinetobacter brings a production of N-deacetyl TAN-588 in a larger amount than the production employing only the microorganism belonging to the genus Empedobacter or the genus Lysobacter.

In order to harvest the objective Antibiotic TAN-588 and/or its N-deacetylated derivative from the resulting culture broth, there are suitably utilized separation means which are normally employed in recovering metabolites produced by a microorganism from its microbial culture. Since the antibiotic TAN-588 and its N-deacetylated derivative behaves like a water-soluble, and is contained mainly in the filtrate of the culture broth, for example, there is advantageously utilized a means which comprises firstly adding a filter aid to the culture broth to remove microbial cells by filtration or centrifugation, contacting the resulting filtrate of the culture broth with a suitable support to adsorb the active ingredient contained in the filtrate and desorbing the active substance with a suitable solvent to conduct fractionation and recovery. As the support, there are advantageously those utilizing the difference in adsorptivity of compounds, such as activated carbon, silica gel, crystalline cellulose and adsorptive resins, those utilizing the difference in functional groups of compounds, such as anion exchange resins and anion exchange cellulose, or those utilizing the difference in a molecular size, such as the medium for gel filtration. In order to elute the objective compound from these supports, for example, aqueous solutions of water-miscible solvents, i.e., aqueous acetone and aqueous alcohols, or aqueous solutions containing acids, alkalies, buffers or inorganic or organic salts are used in suitable combinations, although such combinations varies depending upon the type and characteristics of the support used. Also, the crude material of the present antibiotic obtained by these chromatographic procedures can be subjected to high-performance liquid chromatography (HPLC) for fractionation to perform further purification. Alternatively, the eluate desalted by activated carbon chromatography is concentrated, and the present antibiotic can be recovered from the concentrate by the ion-paired extraction method, i.e. by use of an organic solvent containing quaternary alkylammonium halide.

Referring in more particular to the procedure, as TAN-588 is an acidic substance, when anion exchange resins, such as Dowex-1 (produced by Dow Chemical Co., U.S.A.), Amberlite IRA-68, 400, 402 and 410 (produced by Rohm & Haas, U.S.A.) and Diaion SA-21 and C (produced by Mitsubishi Chemical Industries, Japan), are used as a support, the present antibiotic in the filtrate is adsorbed and eluted for example with aqueous solutions containing salts or acids or buffers. Also, the present antibiotic is adsorbed onto supports, such as anion exchange cellulose, e.g. DE-32 (produced by Whatman Co., U.K.) and DEAE-Cellulose (produced by Braun Co., West Germany), and anion exchange molecular-sieving resins, e.g., DEAE- or QAE-Sephadex (produced by Pharmacia, Sweden), and eluted for example with aqueous solutions containing salts or acids or buffers. For the purpose of removing salts, coloring matters, etc. in these eluates, there are advantageously used activated carbon for chromatographic uses (produced by Takeda Chemical Industries, Ltd., Japan) or adsorptive resins, such as Diaion HP-20 or SP-207 (produced by Mitsubishi Chemical Industries, Japan) and Amberlite XAD-II (produced by Rohm & Haas Co., U.S.A.). The eluted fraction is pulverized through the steps of concentration, lyophilization, etc. In cases in which the resulting powder shows a deteriorated degree of purity, the preparative HPLC method is advantageously applied to further purification. The support, which is usable for this purpose, includes, for example, TSK Gel (produced by Toyo Soda Mfg. Co., Japan) and YMC Gel (produced by Yamamura Chemical Laboratories, Japan), while as the mobile phase, there are used mixed solutions of methanol or acetonitrile, etc. with aqueous acid solutions or buffers, etc. With reference to the quaternary alkyl ammonium halide which is employed in the above-mentioned ion paired extraction method, there are used, for example, tri-n-octylmethylammonium chloride, tetra-n-pentylammonium chloride or n-tetradecyldimethylbenzylammonium chloride, and as the organic solvent, there are normally used, for example, methylene chloride, chloroform or dichloroethane.

Furthermore, as the N-deacetyl TAN-588 has a basic characteristics although it is amphoteric, when cation exchange resins, such as Dowex 50W (Dow Chemical Co., U.S.A.), Amberlite IR-120B (Rohm and Haas, U.S.A.), Diaion SK-110 (Mitsubishi Chemical Industries, Japan), are used as a support, the present antibiotic in the filtrate is adsorbed, and eluted for example with aqueous solutions or buffers containing salts, acids or alkalis.

Also, the present antibiotic is adsorbed onto supports, such as cation exchange molecular-sieving resins, such as CM-Sephadex (Pharmacia, Sweden), and is eluted for example with aqueous solutions or buffers containing salts.

For the purpose of removing the salts, coloring matters, etc. in these eluates, there are advantageously used activated carbon for chromatographic uses or adsorptive resins, such as Diaion SP-207 or HP-20.

The eluated fractions are concentrated, lyophilized and then precipitated. When the resulting powder shows a inferior degree of purity, the preparative HPLC method is advantageously applied to further purification. The support and mobile phase is as the same as those of TAN-588.

TAN-588, in the course of purification, exists in the forms having cations in the used salts or buffers, such as sodium, potassium, lithium, calcium and ammonium ions, attached thereto. In such cases, TAN-588 is isolated as the corresponding salt, when the eluate with its pH remained as such is chromatographed on activated carbon, and is obtained as a free form, when the eluate is adjusted to a pH of 5 to 2, preferably a pH of 4.5 to 3, and chromatographed on activated carbon.

The N-deacety TAN-588 is obtained as an amphoteric substance when it is chromatographed on activated carbon with the eluate of neutral regions. Furthermore, as N-deacetyl TAN-588 has a basic characteristics although it is amphoteric, it can form salts with strong acids. Such strong acids may be mentioned hydrochloric acid, phosphoric acid and trifluoroacetic acid.

TAN-588 as obtained in this manner has two peaks on the reverse-phase HPLC. These peaks are temporarily referred to as A and B, respectively, whereby the phenomena to be described in the following are observed. Collection of the individual peaks A and B by HPLC for fractionation gives A and B in a fairly single form, respectively, but when these are allowed to stand in buffers of pH 3, 5 and 7 at room temperature, A turns into B, with B turning into A, about one hour later at any pH values, thus allowing the once isolated A and B to change into an equilibrium mixture with A:B =about 1:1. Therefore, it is thought impossible to separate TAN-588 itself into A and B by means of the presently known separation techniques. However, the conversion of TAN-588 into the p-nitrobenzyl ester or benzhydryl derivative makes it possible for such a compound to be separated into the A type and B type of the compound, respectively.

As the means of deacetylating Antibiotic TAN-588 or its salt, there are adopted the known deacetylation reactions.

By way of example of such procedures, deacetylation is conducted for example by introducing a p-nitrobenzyl or benzhydryl group into TAN-588 and furthermore removing the acetyl group of TAN-588, followed by elimination of the said p-nitrobenzyl or benzhydryl group, if necessary.

For the purpose of the above-mentioned introduction of a p-nitrobenzyl group, TAN-588 or its salt is reacted with a compound capable of introducing a p-nitrobenzyl group. Examples of the said compound capable of introducing a p-nitrobenzyl group include, for example, p-nitrobenzyl bromide and p-nitrobenzyl chloride.

The amount of the compound capable of introducing a p-nitrobenzyl group to be used ranges from about 1 to 5 equivalents, preferably from about 1 to 2 equivalents. The reaction is preferably carried out in a solvent, and examples of the said solvent include dimethylformamide (DMF), dimethylacetamide (DMAA) and tetrahydrofurane (THF). In the said reaction, for example, triethylamine (Et₃N) and pyridine may be added in quantities of about 0.1 to 0.5 equivalent, preferably about 0.1 to 0.2 equivalent, for the purpose of promoting the reaction.

The reaction temperature is about 0° C. to 40° C., more preferably about 20° C. to 30° C., while the reaction time is about 0.5 to 8 hours, more preferably about 1 to 4 hours. The reaction is preferatlyconducted under stirring.

For the purpose of the above-mentioned introduction of a benzhydryl group, TAN-588 or its salt is reacted with a compound capable of introducing a benzhydryl group. Examples of the said compound capable of introducing a benzhydryl group include, for example, diphenyldiazomethane and diphenylmethyl bromide. The amount of a compound capable of introducing a benzhydryl group to be used ranges from about 1 to 6 equivalents, preferably from about 2 to 4 equivalents. The reaction is preferably carried out in a solvent, and examples of the said solvent include THF, dioxane, ethyl acetate and dichloromethane. In the said reaction, for example, dilute hydrochloric acid, dilute sulfuric acid and dilute phosphoric acid are preferably added in small amounts, e.g. about 0.01 to 1.0 equivalent, to adjust the reaction solution to a pH in the neighborhood of about 1 to 3, preferably about 1.5 to 2.5, for the purpose of promoting the reaction. The reaction temperature is about $-10°$ to $+50°$ C., more preferably 0° C. to 30° C., while the reaction time is about 30 minutes to about 8 hours, more preferably about 1 to 3 hours. The reaction is favorably conducted under stirring.

The ester derivative obtained by the above procedure can be collected by the conventional separation or purification means. By way of example of the said means, the objective compound is extracted into the organic layer by use of e.g. dichloromethane or chloroform, and the extract is concentrated, followed by addition of the resulting concentrate to ether, hexane, etc. to allow the said ester derivative to separate out in the form of a crystalline powder. This ester derivative is separated into two components by the silica gel chromatographic method, but may be used as a mixture when the subsequent reaction is stepped forward to.

Furthermore, the p-nitrobenzyl ester or benzhydryl derivative of TAN-588 as obtained by the above procedure is subjected to deacetylation.

Examples of the said deacetylation include the imino ether method, solvolysis method and hydrolysis method by use of enzymes.

In cases in which the imino ether method is used, for example, the starting compound is reacted with phosphorus pentachloride, phosgene, phosphorus trichloride, phosphorus oxychloride, etc. The above-mentioned reagents are preferablyused in about 1 to 5 equivalents, more preferably about 1.5 to 3 equivalents. The said reaction is conveniently carried out in the presence of a solvent, such as methylene chloride, dichloroethane, choroform, carbon tetrachloride and trichloroethane. For the purpose of promoting the reaction, it is preferable to use for example pyridine, N,N-dimethylaniline, triethylamine, aniline or toluidine in excessive quantities, e.g. about 3 to 20 equivalents, more preferably about 5 to 10 equivalents.

The said deacetylation reaction is desirably carried out at a reaction temperature of about $-30°$ C. to 0° C., more preferably $-15°$ C. to $-5°$ C., for a length of reaction time of about 15 minutes to 8 hours, more preferably about 30 minutes to 2 hours. The reaction is conveniently carried out under stirring.

In order to convert imino chloride formed as an intermediate into imino ether, an excess of methanol is added to the reaction solution, and the mixture is stirred at a temperature of about $-30°$ C. to 0° C., preferably about $-15°$ C. to $-5°$ C., for a period of time of about 15 minutes to 2 hours, preferably about 30 minutes to 1 hour, followed by further stirring at about 10° C. to 40° C., preferably about 20° C. to 30° C., for about 30 minutes to 2 hours, for the termination of the reaction. Furthermore, dilute hydrochloric acid is added to the reaction solution to severe the C-N linkage, whereby the reaction temperature is about 10° C. to 40° C., preferably about 20° C. to 30° C., and the reaction time is about 15 minutes to 2 hours, preferably about 30 minutes to 1 hour.

In employing the solvolysis method, for example, the starting compound is dissolved in methanol, ethanol or a mixture thereof with water, and the reaction is allowed to proceed at about 20° C. to the refluxing temperature, preferably about 50° C. to the refluxing temperature, for about 0.5 to 30 hours, preferably about 2 to 8 hours.

The reaction solution thus obtained is neutralized, and the reaction product is extracted with an organic solvent immiscible with water, for example, methylene chloride, diethyl ether or ethyl acetate, followed by concentration of the extract to yield the p-nitrobenzyl or benzhydryl derivative of deacetylated TAN-588.

In order to eliminate the ester group as a final step, for example, the acid hydrolysis method, catalytic reduction method, etc. are employed In cases in which the acid hydrolysis method is employed, an acid, such as trifluoroacetic acid, formic acid and hydrochloric acid, is used at a rate of about 3 to 20 equivalents against the starting compound to allow the reaction to proceed. Also, it is preferred to add anisole of about 1 to 5 equivalents, preferably 2 to 4 equivalents. In the said reaction, as the solvent, there may be used for example methylene chloride, chloroform, THF, ethyl acetate, etc.

The reaction temperature is about −30° C. to 0° C., more preferably −20° C. to −10° C., and the reaction time is about 0.5 to 8 hours, more preferably about 1 to 4 hours.

In employing the catalytic reduction method, as the catalyst, there may be used for example palladium, platinum, their oxides, etc. to allow the reaction to proceed in a stream of hydrogen.

The reaction temperature is about 0° C. to 50° C., more preferably about 10° C. to 40° C., while the reaction time is about 0.1 to 6 hours, more preferably about 0.2 to 2 hours.

The free carboxylic acid derivative thus produced can be separated, collected and purified by removing impurities in the reaction solution by filtration or chromatographic method, such as those utilizing for example activated carbon or adsorptive resins, followed by concentration, lyophilization, etc.

In each of the above steps, and when the resulting compound is a mixture of isomers, for example, column chromatography, such as the methods utilizing silica gel, Sephadex LH-20 (produced by Pharmacia Co., Sweden), Diaion HP-20, etc. as a support, or recrystallization method and preparative reverse phase chormatography [examples of the support: YMC Gel, TSK Gel; examples of the mobile phase: buffers or buffers containing methanol or acetonitrile] for fractionation can permit the separation into individual isomeric components.

The TAN-588 sodium salt (an equilibrium mixture of A and B) as obtained in Example 1 to be described hereinafter showed physico-chemical properties which are as follows:

(1) Appearance: White powder.

(2) Specific rotation: $[\alpha]_D^{23} 19.0° \pm 10°$ (c=0.5, in water).

(3) Elemental analysis for the compound being constituted of the elements, C, H, N, O and Na (%): for a sample being dried over phosphorus pentoxide at 40° C. for 6 hours.

| Found | Calcd.* |
|---|---|
| C, 38.5 ± 2.0 | C, 39.61 |
| H, 4.5 ± 1.0 | H, 3.99 |
| N, 9.1 ± 1.5 | N, 9.24 |
|  | O, 39.58 |
| Na, 6.9 ± 1.5 | Na, 7.58 |

*calculated assuming that 0.5 mole of water of adhesion is contained.

(4) Content of adhesive water: 3.0±1.5 % (by the thermoglavimetric method).

(5) The molecular ion peak according to the SIMS method is as follows: m/e 611(2M+Na)+, 317(M+Na)+, 295(M+H)+.

(6) Molecular formula: $C_{10}H_{11}N_2O_7Na$.

(7) Ultraviolet absorption (UV) spectrum (in water): FIG. 1 $\lambda_{max}$ 216 nm ($E_{1\ cm}^{1\%}$ = 130 shoulder).

(8) Infrared absorption (IR) spectrum (KBr method):
The infrared absorption spectrum (FIG. 2), recorded as KBr disc, demonstrates the following principal absorption peaks (in wave number): 3450, 1780, 1730, 1660, 1550, 1385, 1320, 1290, 1260, 1200, 1120, 1040, 980, 910, 810, 770, 690, 600, 540 cm$^{-1}$.

(9) $^{13}$C-Nuclear magnetic resonance (NMR) spectrum (100 MHz, in deuterium oxide): The following peaks are observed. 182.02(s), 177.30(s), 173.79(s), 173,30(s), 173.25(s), 172.58(s), 96.97(s), 96.92(s), 74.27(t), 72.68(t), 55.57(d), 55.34(d), 31.92(t), 31.08(t), 30.98(t), 24.58(q), ppm (wherein s; singlet, d; doublet, t; triplet, and q; quartet).

(10) Circular dichroism (CD) spectrum (in water):
The negative Cotton effect is revealed at 232±3 nm.

(11) Solubility:
Soluble in: Water, dimethylsulfoxide.
Sparingly soluble in: Ethyl acetate, chloroform, diethyl ether.

(12) Color reaction:
Positive: Ninhydrin reaction
Negative: Greig-Leaback reaction, Sakaguchi reaction, Ehrlich reaction, Barton reaction, Dragendorff's reaction.

(13) Amino acid analysis: Hydrolysis in 6N-hydrochloric acid at 105° C. for 20 hours allows the detection of serine as the known amino acid.

(14) Stability: Stable in an aqueous solution at pH 5, slightly stable at pH 3 and 7, and unstable at pH 9.

(15) Thin-layer chromatography (Cellulose f, produced by Tokyo Kasei Co. of Japan):

| Solvent system | Rf value |
|---|---|
| Acetonitrile:water (4:1) | 0.33 |
| Butanol:acetic acid:water (1:1:1) | 0.77 |
| Acetonitrile:3% ammonium sulfate (4:1) | 0.28 |

(16) Discrimination among acidity, neutrality and basicity:
Neutral substance.

(17) HPLC (support: UMC A-312, produced by Yamamura Chemical Laboratories, Japan, mobile phase: 4 % methanol/0.01M phosphate buffer (pH 6.3), 2 ml/min.):
Rt=4.3 and 4.8 (min).

The physico-chemical properties of TAN-588-P-nitrobenzyl ester (a mixture of A type and B type compounds) obtained in Example 4 which appears hereinafter are shown below.

(1) Appearance: white powder.

(2) Specific rotation: $[\alpha]_D^{23} \pm 16.3° \pm 5°$ (C=0.485, in CHCl$_3$).

(3) Molecular weight: 407 (according to SIMS method).

(4) Elemental analysis: Calcd.: C,50.13; H,4.21; N,10.32; O,35.35. Found: C,50.26; H,4.32; N,10.31.

(5) Molecular formula: C$_{17}$H$_{17}$N$_3$O$_9$.

(6) UV spectrum: $\lambda_{max}^{MeOH}$ nm (E$_1$ $_{cm}$$^{1\%}$)=262±2 (281±20), 214±2 (278±20, shoulder).

(7) IR spectrum: KBr method, FIG. 3 3400, 3080, 2960, 1805, 1760, 1680, 1610, 1520, 1450, 1380, 1350, 1270, 1180, 1105, 1050, 1015, 970, 905, 850, 740, 690, 600, 540 cm$^{-1}$.

(8) $^1$H-NMR spectrum: 90 MHz, in CDCl$_3$ δ ppm J(Hz) 2.05(3H,s), 2.3–3.3(4H,m), 4.10(1H,m), 4.5–5.1(2H,m), 5.35(2H,s), 6.25(1H,d,like), 7.55(2H,dd like), 8.27(2H,d,like).

(9) TLC:
Carrier: silica gel (Merck, West Germany)
Developping solvent: chloroform: methanol (19:1)
Rf value, 0.25 and 0.32

(10) Acidic, neutral or basic: neutral substance.

The physico-chemical properties of TAN-588A-p-nitrobenzyl ester obtained in Example 4 which appears hereinafer are shown below.

(1) Appearance: white powder.

(2) Specific rotation: $[\alpha]_D^{20}+97.3° \pm 15°$ (C=0.48 in CHCl$_3$).

(3) Molecular weight: 407 (according to SIMS method).

(4) Elemental analysis: Calcd.: C,50.13; H,4.21; N,10.32; O,35.35. Found: C,50.20; H,4.22; N,10.13.

(5) Molecular formula: C$_{17}$H$_{17}$N$_3$O$_9$.

(6) UV spectrum: $\lambda_{max}^{MeOH}$(E$_1$ $_{cm}$$^{1\%}$)=262±2 nm (280±30), 214±2nm (276±30, shoulder).

(7) $^{13}$C-NMR spectrum:(100 MHz, CDCl$_3$), 173.70(s), 171.53(s), 170.72(s), 165.09(s), 148.06(s), 141.38(s), 128.86(d), 123.91(d), 91.82(s), 71.60(t), 67.29(t), 53.00(d), 29.09(t), 27.49(t), 22.64(q), ppm.

(8) IR spectrum: KBr method, FIG. 4 3400, 3080, 2950, 1805, 1775, 1760, 1680, 1610, 1530, 1450, 1380, 1350, 1300, 1275, 1190, 1105, 1060, 1020, 980, 910, 850, 740, 700, 600, 540 cm$^{-1}$.

(9) TLC:
Carrier: silica gel (Merck, West Germany)
Developping solvent: chloroform: methanol (19:1)
Rf value: 0.25

(10) Acidic, neutral or basic: neutral substance.

The physico-chemical properties of TAN-588B-p-nitrobenzyl ester obtained in Example 4 which appears hereinafter are shown below.

(1) Appearance: white powder.

(2) Specific rotation: $[\alpha]_D^{20}-64.5° \pm 15°$ (C=0.50, in CHCl$_3$).

(3) Molecular weight: 407 (according to SIMS method).

(4) Elemental analysis: Calcd.: C,50.13; H,4.21; N,10.32; O,35.35. Found: C,50.10; H,4.21; N,10.15.

(5) Molecular formula: C$_{17}$H$_{17}$N$_3$O$_9$.

(6) UV spectrum: $\lambda_{max}^{MeOH}$ (E$_1$ $_{cm}$$^{1\%}$)=262±2 nm (282±30) 214±2 nm (280±30, shoulder).

(7) $^{13}$C-NMR spectrum: (100 MHz, CDCl$_3$), 173.59(s), 170.86(s), 170.61(s), 165.06(s), 148.12(s), 141.24(s), 128.96(d), 123.96(d), 91.69(s), 74.60(t), 67.39(t), 51.94(d), 29.11(t), 27.38(t), 22.67(q), ppm.

(8) IR spectrum: KBr method, FIG. 5 3400, 3090, 2950, 1805, 1760, 1680, 1610, 1530, 1450, 1380, 1355, 1270, 1180, 1105, 1055, 1015, 965, 910, 835, 740, 695, 600, 540 cm$^{-1}$.

(9) TLC: the same conditions as those of p-nitrobenzyl ester of TAN-588A Rf value, 0.32.

(10) Acidic, neutral or basic: neutral substance.

The physico-chemical properties of TAN-588 benzhydryl ester (a mixture of A and B) obtained in Example 5 which appears hereinafter are shown below.

(1) Appearance: colorless crystal.

(2) Melting point: 153°–155° C. (Decomposition).

(3) Specific rotation: $[\alpha]_D^{23}+9.2° \pm 5°$ (C=0.52 in CHCl$_3$).

(4) Molecular weight: m/z 438(M+)(EI-MS method).

(5) Elemental analysis: Calcd.: C,63.01; H,5.06; N,6.39; O,25.54. Found: C,62.83; H,5.32; N,6.28.

(6) Molecular formula: C$_{23}$H$_{22}$N$_2$O$_7$.

(7) UV spectrum:in methanol $\lambda_{max}$ 220±2 nm (E$_1$ $_{cm}$$^{1\%}$=285±50, shoulder) and 250–260 nm (E$_1$ $_{cm}$$^{1\%}$=28±10, shoulder).

(8) IR spectrum: KBr method, FIG. 6 3380, 3080, 3050, 2960, 1800, 1780, 1750, 1705, 1690, 1600, 1590, 1540, 1500, 1460, 1380, 1310, 1280, 1190, 1110, 1060, 980, 920, 880, 750, 710, 700, 650, 630, 610, 570, 550, 470 cm$^{-1}$.

(9) $^1$H-NMR spectrum: 90 MHz, in CDCl$_3$, δ ppm J(Hz) 1.97(3H,s), 2.1–3.5(4H,m), 3.8–4.2(1H,m), 4.5–5.1(2H,m), 6.1–6.4(1H,br), 6.97(1H,s), 7.3–7.4(10H,m) (m: multiplet, br: broad, H: proton).

(10) TLC: the same conditions as those of A type compound (mentioned below) Rf value, 0.58 and 0.65.

(11) Acidic, neutral or basic: nuetral substance.

The physico-chemical properties of TAN-588 benzhydryl ester (A type compound) and TAN-588 benzhydryl ester (B type compound) obtained in Example 5 which appears hereinafter are shown below.

A type compound (1) Appearance: colorless crystal.

(2) Melting point: 97°–135° C. (gradually foaming and decomposing).

(3) Specific rotation: $[\alpha]_D^{21}+44.2° \pm 10°$ (C=0.505, in CHCl$_3$).

(4) Molecular weight: Molecular ion peak according to EI-MS method m/z 438 (M+).

(5) Elemental analysis: Calcd.: C,63.01; H,5.06; N,6.39; O,25.54. Found: C,62.62; H,5.06; N,6.32.

(6) Molecular formula: C$_{23}$H$_{22}$N$_2$O$_7$.

(7) UV spectrum: in methanol $\lambda_{max}$ 220±2 nm (E$_1$ $_{cm}$$^{1\%}$=290±50, shoulder) and 250–260 nm (E$_1$ $_{cm}$$^{1\%}$=30±10, shoulder).

(8) IR spectrum: KBr method, FIG. 7 3380, 3080, 3050, 1800, 1780, 1760, 1685, 1540, 1500, 1450, 1380, 1310, 1280, 1190, 1110, 1050, 980, 920, 880, 750, 710, 650, 610, 550 cm$^{-1}$.

(9) $^1$H-NMR spectrum: 100 MHz, in a mixed solvent of CDCl$_3$ and d$_6$-DMSO, δ ppm J(Hz) 1.98(3H,s), 2.2–3.4(4H,m), 4.10(1H,dd,J=8,10), 4.4–5.0 (2H,m), 6.93(1H,s), 7.3–7.5(10H,m), 8.27(1H,d,J=7).

(10) TLC Carrier, silica gel (Merck, West Germany) Developping solvent, ethyl acetate Rf value, 0.58.

(11) Acidic, neutral or basic: neutral substance.

B type compound (1) Appearance: colorless crystal.

(2) Melting point: 157°–160° C. (Decomposition).

(3) Specific rotation: $[\alpha]_D^{21}-28.8° \pm 10°$ (C=0.5, in CHCl$_3$).

(4) Molecular weight: m/z 438(M+)(EI-MS method).

(5) Elemental analysis: Calcd.: C,63.01; H,5.06; N,6.39; O,25.54. Found: C,63.11; H,5.13; N,6.30.

(6) Molecular formula: $C_{23}H_{22}N_2O_7$.

(7) UV spectrum: in methanol $\lambda_{max}$ 220±2 nm ($E_1{}_{cm}{}^{1\%}$=300±50, shoulder) 250–260 nm ($E_1{}_{cm}{}^{1\%}$=26±10, shoulder).

(8) IR spectrum: KBr method, FIG. 8 3400, 3080, 3050, 1815, 1780, 1735, 1705, 1540, 1460, 1380, 1290, 1265, 1190, 1060, 980, 920, 880, 760, 715, 610, 550 cm$^{-1}$.

(9) $^1$H-NMR spectrum: 100 MHz, in CDCl$_3$ δ ppm J (Hz), 1.98(3H,s), 2.2–3.4(4H,m), 4.03(1H,dd,J=8,10), 4.6–5.2 (2H,m), 6.32(1H,d,J=5), 6.96(1H,s), 7.2–7.5(10H,m).

(10) TLC: (the same conditions as those of the A type compound) Rf value, 0.65.

(11) Acidic, neutral or basic: neutral substance.

The physico-chemical properties of benzhydryl ester (a mixture of A type and B type compounds) of N-deacetyl TAN-588 obtained in Example 6 which appears hereinafter are shown below.

(1) Appearance: white powder.

(2) Specific rotation: $[\alpha]_D{}^{25}$ −15.2°±5° (C=0.5, in CHCl$_3$).

(3) Molecular weight: m/z 396(M$^+$)(EI-MS method)

(4) Elemental analysis: Calcd.: C,63.63; H, 5.09; N,7.07; O,24.22. Found : C,63.63; H,5,05; N,7.02.

(5) Molecular formula: $C_{21}H_{20}N_2O_6$.

(6) UV spectrum: in methanol $\lambda_{max}$ 220±2 nm ($E_1{}_{cm}{}^{1\%}$=336±50, shoulder) 250–260 nm ($E_1{}_{cm}{}^{1\%}$32±10, shoulder).

(7) IR spectrum: KBr method, FIG. 9 3400, 3050, 2970, 1800, 1780, 1740, 1600, 1500, 1460, 1305, 1270, 1190, 1110, 1060, 980, 920, 880, 850, 750, 710, 650, 620, 605 cm$^{-1}$.

(8) $^1$H-NMR spectrum: 90 MHz, in CDCl$_3$ δ ppm J (Hz), 2.2–3.5(4H,m), 3.7–4.0(2H,m), 4.4–4.6(1H,m), 6.97(1H,s), 7.2–7.4(10H,m).

(9) HPLC: Model 6000A/660/440 (Waters Assoc., U.S.A.) Column, YMC-Pack A-312 (Yamamura Chemical Laboratories, Japan) Mobile phase, 65% methanol/0.01M phosphate buffer (pH 6.3) 2 ml/min, Rt: 5.3, 5.6 min.

(10) Color reaction:
Positive: Ninhydrin
Negative: Ferric chloride.

(11) Acidic, neutral or basic: basic substance.

The physico-chemical properties of N-deacetyl TAN-588 (a mixture of A type and B type compounds) obtained in Example 7 which appears hereinafter are shown below.

(1) Appearance: white powder.

(2) Specific rotation: $[\alpha]_D{}^{25}$ −11°±5° (C=0.1, in water).

(3) Molecular weight: m/z 231 (M+H)$^+$ (FD-MS method).

| (4) Elemental analysis: | |
|---|---|
| Found | Calcd.* |
| C,40.42 | C,40.17 |
| H, 4.36 | H, 4.64 |
| N,11.65 | N,11.71 |
| | O.43.48 |

*The value is calculated as the sample contains 0.5 moles of water (5) Molecular formula: $C_8H_{10}N_2O_6$(0.5 H$_2$O).

(6) UV spectrum: in water $\lambda_{max}$ 221±2 nm ($E_1{}_{cm}{}^{1\%}$154±20).

(7) IR spectrum: KBr method, FIG. 10 Principal absorption 3450, 3220, 2960, 2900, 1800, 1760, 1740, 1670, 1580, 1420, 1390, 1370, 1310, 1250, 1200, 1120, 1050, 1030, 980, 950, 920, 810, 770, 720, 690, 610, 540 cm$^{-1}$.

(8) $^1$H-NMR spectrum: 400 MHz, in D$_2$O The following signals are observed. δppm J (Hz) 2.52(1H,m), 2.72(1H,m), 2.91(1H,m), 3.08(1H,m), 4.35(1H,m), 4.56(1H,m), 4.80(1H,m).

(9) CD spectrum: in water The negative Cotton effect is revealed at 233±3 nm.

(10) Solubility:
Soluble: water
Sparingly soluble: dimethylsulfoxide, ethyl acetate, diethylether

(11) HPLC: machine, column and flow rate are the same conditions as those of deacetylated benzhydryl ester (a mixture of A type and B type compounds) Mobile phase, 0.01 M phosphate buffer (pH 6.3) Rf: 3.1 and 3.3 min.

(12) Color reaction:
Positive: Ninhydrin, iodine
Negative: Ferric chloride

(13) Acidic, neutral or basic: amphoteric substance.

The physico-chemical properties of N-deacetyl TAN-588 (A type compound) obtained in Example 8 which appears hereinafter are shown below.

(1) Appearance: colorless crystal.

(2) Melting point: 177°–181° C. (Decomposition).

(3) Specific rotation: $[\alpha]_D{}^{25}$ +124°±20° (C=0.1 in water).

(4) Molecular weight: m/z 231 (M+H)$^+$ (FD-MS method).

| (5) Elemental analysis: | |
|---|---|
| Found | Calcd. |
| C, 41.57 | C, 41.75 |
| H, 4.39 | H, 4.38 |
| N, 12.11 | N, 12.17 |
| | O, 41.71 |

(6) Molecular formula: $C_8H_{10}N_2O_6$.

(7) UV spectrum:in water $\lambda_{max}$ 221±2 nm ($E_1{}_{cm}{}^{1\%}$=151±20).

(8) IR spectrum: KBr method, FIG. 11 Principal absorption 3450, 3220, 2950, 2900, 1800, 1735, 1660, 1580, 1440, 1420, 1400, 1360, 1340, 1310, 1280, 1200, 1160, 1110, 1050, 1025, 980, 940, 920, 810, 700, 710 690, 600, 540 cm$^{-1}$.

(9) $^1$H-NMR spectrum: 400 MHz in D$_2$O, The following signals are observed. δ ppm J (Hz) 2.52(1H,m), 2.72(1H,m), 2.91(1H,m), 3.08(1H,m), 4.34(1H,m), 4.55(1H,m), 4.78(1H,m).

(10) CD spectrum:in water The negative Cotton effect is revealed at 238±3 nm.

(11) Solubility
Soluble in: Water
Sparingly soluble in: dimethylsulfoxide, ethyl acetate, chloroform, diethyl ether.

(12) HPLC: the same conditions as those of the mixture of A type and B type compounds Rt, 3.3 min.

(13) Acidic, neutral or basic: Amphoteric substance.

The physico-chemical properties of N-deacetyl TAN-588 (B type compound) obtained in Example 9 which appears hereinafter are shown below. Appearance: white powder (1) Appearance: white powder.

(2) Molecular: m/z 231 (M+H)$^+$ (FD-MS method).

(3) Elemental analysis

| Found | Calcd.* |
|---|---|
| C, 40.98 | C, 40.17 |
| H, 4.88 | H, 4.64 |
| N, 12.17 | N, 11.71 |
|  | O, 43.48 |

*The value is calculated as the sample contains 0.5 mole of water (4) Molecular formula: $C_8H_{10}N_2O_6(0.5\ H_2O)$.

(5) UV spectrum: in water $\lambda_{max}$ 221±2 nm ($E_1\ cm^{1\%}=133\pm20$).

(6) IR spectrum: KBr method, FIG. 12 Principal absorption 3440, 2980, 1800, 1760, 1670, 1570, 1520, 1390, 1290, 1250, 1190, 1090, 1050, 990, 920, 810, 760, 720, 690 $cm^{-1}$.

(7) $^1$H-NMR spectrum: 400 MHz in $D_2O$ The following signals are observed. δ ppm J(Hz) 2.52(1H,m), 2.72(1H,m), 2.90(1H,m), 3.08(1H,m), 4.44(1H,m), 4.68(1H,m), 4.86(1H,m).

(8) CD spectrum in water The negative Cotton effect is revealed at 224±2 nm.

(9) Solubility
Soluble in: Water
Sparingly soluble in: dimethylsulfoxide, ethyl acetate, chloroform, diethyl ether

(10) HPLC: The same conditions as those of the mixture of A type and B type compounds Rt, 3.1 min.

(11) Acidic, neutral or basic: Amphoteric substance.

Based on said physico-chemical properties and reaction process, it is assumed that TAN-588 has an acetyl group which is bound to a nitrogen atom in its molecule and has a carboxyl group in its molecule.

Then, the biological characteristics of TAB-588 be described. The TAN-588 sodium salt exhibits the antimicrobial spectrum against various microorganisms as shown in Table 1.

TABLE 1

| Test microorganism | Minimal inhibitory concentration (μg/ml) (Note 1) |
|---|---|
| Staphylococcus aureus FDA 209P | 3.13 |
| Micrococcus luteus IFO 12708 | 0.39 |
| Bacillus subtilis NIHJ PCI 219 | 3.13 |
| Bacillus cereus FDA 5 | 12.5 |
| Escherichia coli NIHJ JC 2 | 50 |
| Salmonella typhimurium IFO 12529 | 50 |
| Citrobacter freundii IFO 12681 | 100 |
| Klebsiella pneumoniae IFO 3317 | 100 |
| Serratia marcescens IFO 12648 | 50 |
| Proteus mirabilis ATCC 21100 | 25 |
| Proteus vulgaris IFO 3988 | 25 |
| Proteus morganii IFO 3168 | 100 |
| Pseudomonas aeruginosa IFO 3080 | >100 |
| Alcaligenes faecalis IFO 13111 | 50 |
| Acinetobacter calcoaceticus IFO 13006 | 25 |

(Note 1): As the culture medium, there was used a medium consisting of 17.5 g of Bacto Antibiotic Medium 3 (produced by Difco Laboratories of U.S.A.), 5.0 g of Bacto Yeast extract (produced by Difco Laboratories of U.S.A.), 2.0 g of Bacto Agar (produced by Difco Laboratories of U.S.A.) and 1000 ml of distilled water (without adjustment of pH), while as the bacterial inoculation solution, there was used about $10^6$ colony forming units/ml.

The TAN-588 sodium salt demonstrated the therapeutic effect in the experimental mouse infection as shown in Table 2.

TABLE 2

| Infectious microorganism | Route of administration | $ED_{50}$ (mg/kg) |
|---|---|---|
| Staphylococcus aureus 308A-1 | Subcutaneous | 25.0 |

Furthermore, the TAN-588 sodium salt, even when administered subcutaneously at a dose of 400 mg/kf, was found to produce no acute toxicity.

Described below are the biological characteristics of N-deacetyl TAB-588 (a mixture of the A type and a B type compounds). It is added that a mixture of the said A type and B type compounds is identical in bilogical characteristics to the A type and B type compounds.

The antimicrobial spectrum of N-deacetyl TAN-588 against various microorganisms is as shown in Table 3.

TABLE 3

| Test microorganism | Minimal inhibitory concentration (μg/ml) (Note 1) |
|---|---|
| Staphylococcus aureus FDA 209P | 50 |
| Micrococcus luteus IFO 12708 | 6.25 |
| Bacillus subtilis NIHJ PCI 219 | 12.5 |
| Bacillus cereus FDA 5 | 50 |
| Escherichia coli NIHJ JC 2 | 25 |
| Salmonella typhymurium IFO 12529 | 50 |
| Citrobacter freundii IFO 12681 | 50 |
| Klebsiella pneumoniae IFO 3317 | 100 |
| Serratia marcescens IFO 12648 | 25 |
| Proteus mirabilis ATCC 21100 | 100 |
| Proteus vulgaris IFO 3988 | 100 |
| Proteus morganii IFO 3168 | >100 |
| Pseudomonas aeruginosa IFO 3080 | 50 |
| Alcaligenes faecalis IFO 13111 | 100 |
| Acinetobacter calcoaceticus IFO 13006 | 50 |

(Note 1): As the culture medium, there was used a medium consisting of 17.5 g of Bacto Antibiotic Medium 3 (produced by Difco Laboratories, U.S.A.), 50 g of Bacto Yeast extract (produced by Difco Laboratories, U.S.A.), 20 g of Bacto Agar (produced by Difco Laboratories, U.S.A.) and 1000 ml of distilled water (without adjustment of pH), while as the bacterial inoculation solution, there was employed about $10^6$ colony forming unit/ml.

Also, N-deacetyl TAN-588 is stable to various β-lactamase; it was examined for the stabilities against 2 kinds of β-lactamases, with the use of Escherichia coli PG 8 as a test microorganism, and the results asre shown in Table 4.

TABLE 4

| β-Lactamase | Deacetylated TAN-588 | PCG | CPC | CMC |
|---|---|---|---|---|
| Without addition | 22.5 | 22 | 33 | 34 |
| Penicillinase*1 | 24.5 | —*3 | 32 | 34 |
| Cephalosporinase*2 | 21.5 | — | — | — |

*1Derived from Bacillus cereus, produced by Calbio Chemical Co. of U.S.A.).
*2Derived from Enterobacter cloacae.
*3No inhibition zone indicated.

As described in the above, TAN-588, its p-nitrobenzyl or benzhydryl-ester derivative or their deacetylated derivatives [hereinafter referred to collectively as "Compound (I)"], or salts thereof exhibit antimicrobial activities against Gram-positive and Gram-negative microorganisms, and are low in toxicity. Consequently, the Compounds (I) of the present invention or their salts can be used for the treatment of bacterial infections in mammals [e.g., rats, mice, dogs, cats, domestic animals (horses, etc.), human, etc.], fowls, etc.

In using the Compounds (I) of the present invention or their salts as a therapeutic agent for microbial infections, they can be administered, as admixture with pharmacologically acceptable carriers, excipients, diluents, etc., orally as tablets, capsules, etc. or parenterally as injectable solutions, etc. Examples of the diluent which is usable in formulating into injectable solutions include isotonic saline solution, etc. Examples of the carrier which is useful in formulating into capsules include for example lactose, etc. Their dosage levels are about 5 to 50 mg/kg/day as the Compound (I), preferably about 10 to 25 mg/kg/day, for the preparations for oral administration, and about 2.5 to 25 mg/kg/day as the Compound (I), preferably about 5 to 20 mg/kg/day, for the preparations for parenteral administration.

Also, the Compounds (I) as obtained according to the present invention or their salts can be employed as an antimicrobial agent and disinfectant. They can be utilized, for example, as a solution preparation formulated by dissolving in distilled water to a concentration of 0.01 to 0.1 W/V % as the Compound (I) or as an ointment containing 0.2 to 20 mg as the Compound (I) per g, preferably 1 to 10 mg, formulated with white petrolatum or lanolin used as a base, for the sterilization of disinfection of hands, feet, eyes, ears, etc. of man and animals.

The Compounds (I) as obtained by the method according to the present invention are highly promising compounds as an intermediate for the synthesis of new drugs.

The above-described physico-chemical properties and biological characteristics has led the present inventors to the conclusion that the Compounds (I) are novel antibiotics.

BRIEF DESCRIPTION OF THE DRAWING

FIGS. 2, 3, 4, 5, 6, 7, 8, 9, 10, 11 and 12 show the absorption spectra in the ihfrared region of TAN-588 (an equilibrium mixture of A and B), p-nitrobenzyl ester of TAN-588 (a mixture of A and B), p-nitrobenzyl ester (A type) of TAN-588, p-nitrobenzyl ester (B type) of TAN-588, benzhydryl ester (a mixture of A and B) of TAN-588, benzhydryl ester (A type) of TAN-588, benzhydryl ester (B type) of TAN-588, benzhydryl ester (a mixture of A and B) of N-deacetyl TAN-588, benzhydryl ester (A type) of N-deacetyl TAN-588, benzhydryl ester (B type; of N-deacetyl TAN-588, N-deacetyl TAN-588 (a mixture of A and B), N-deacetyl TAN-588 (A type) and N-deacetyl TAN-588 (B type), respectively.

Figure 1:
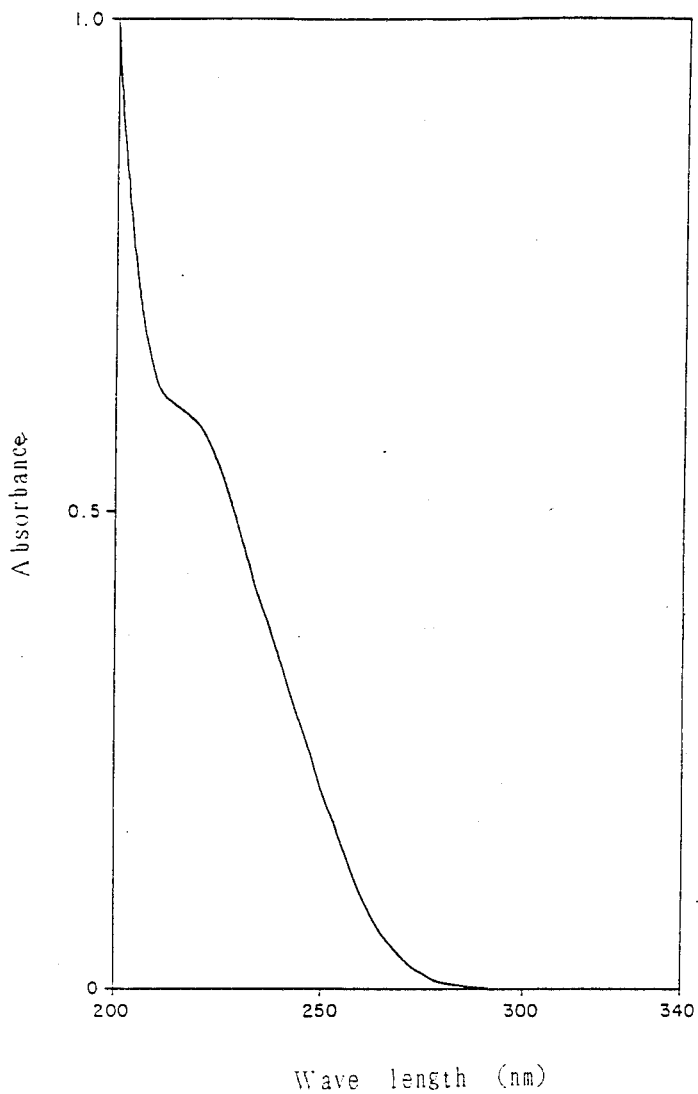
FIG. 1 shows the absorption spectrum in the ultraviolet region of TAN-588 (an equilibrium mixture of A and B).
Figure 2:
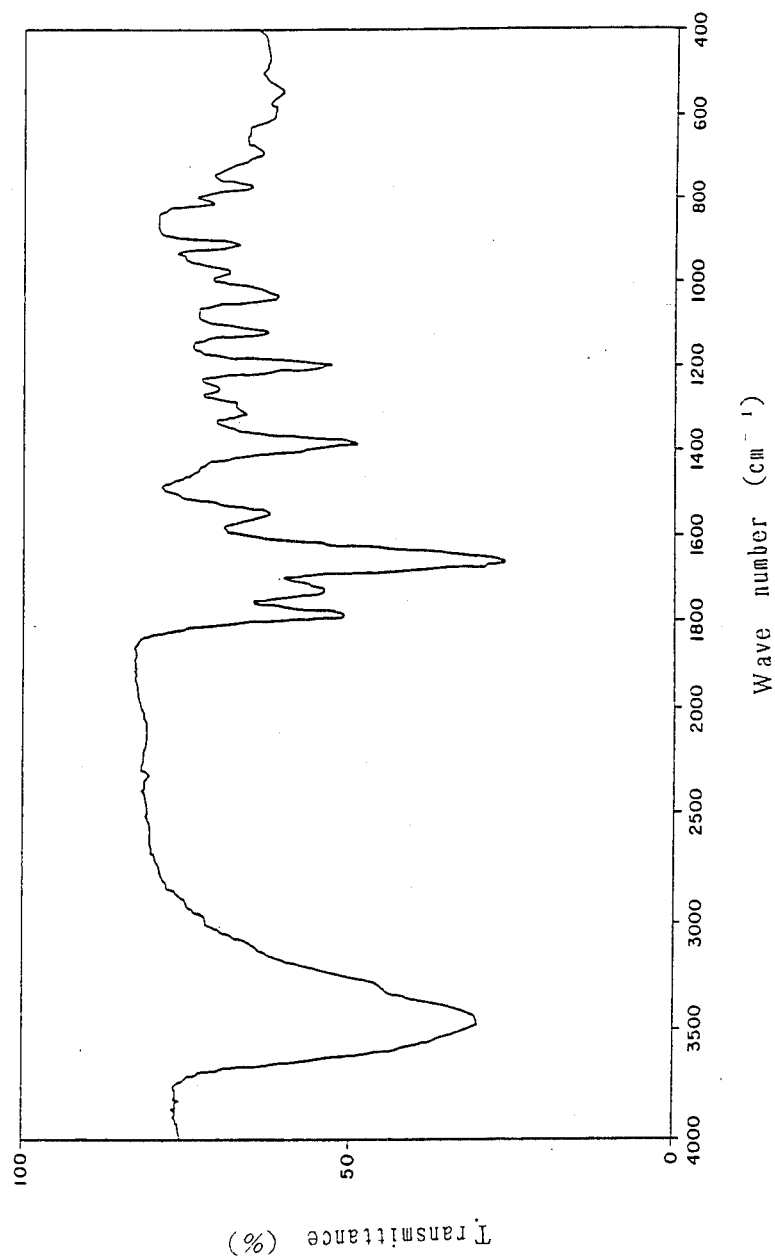
Figure 3:
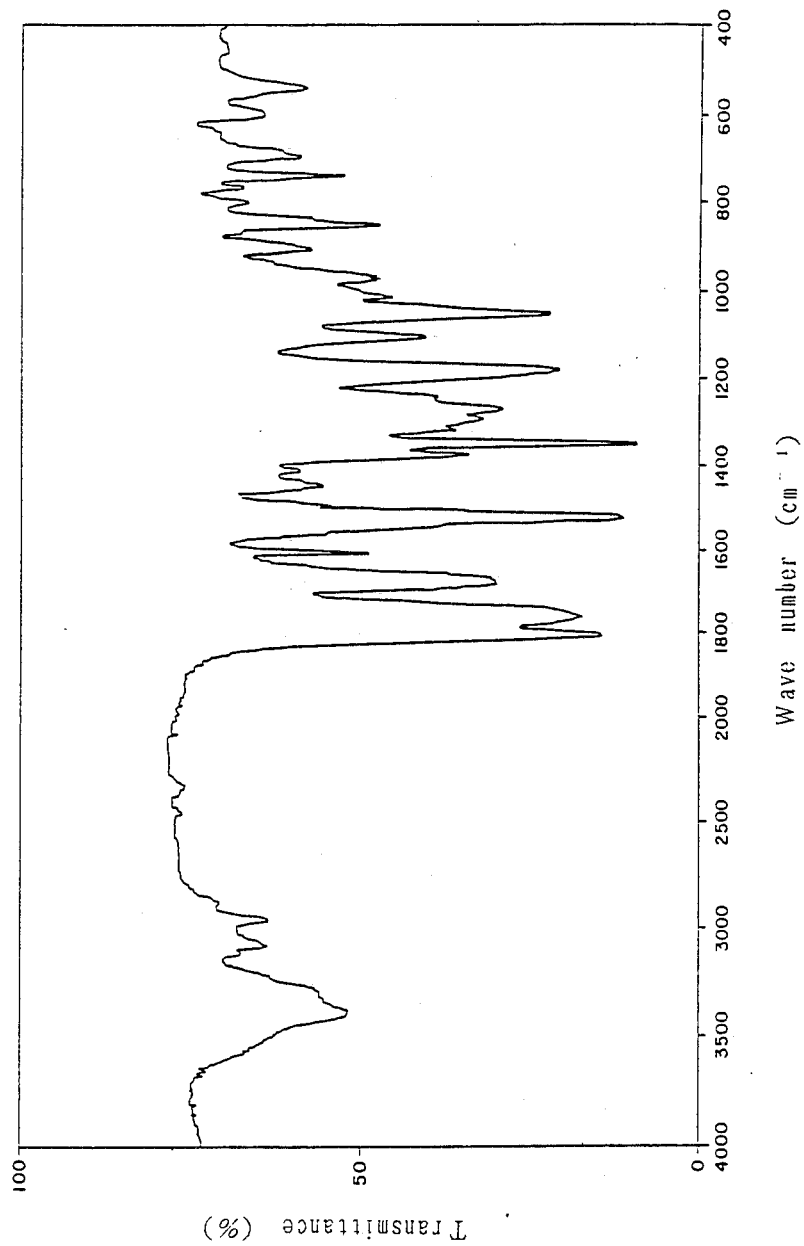
Figure 4:
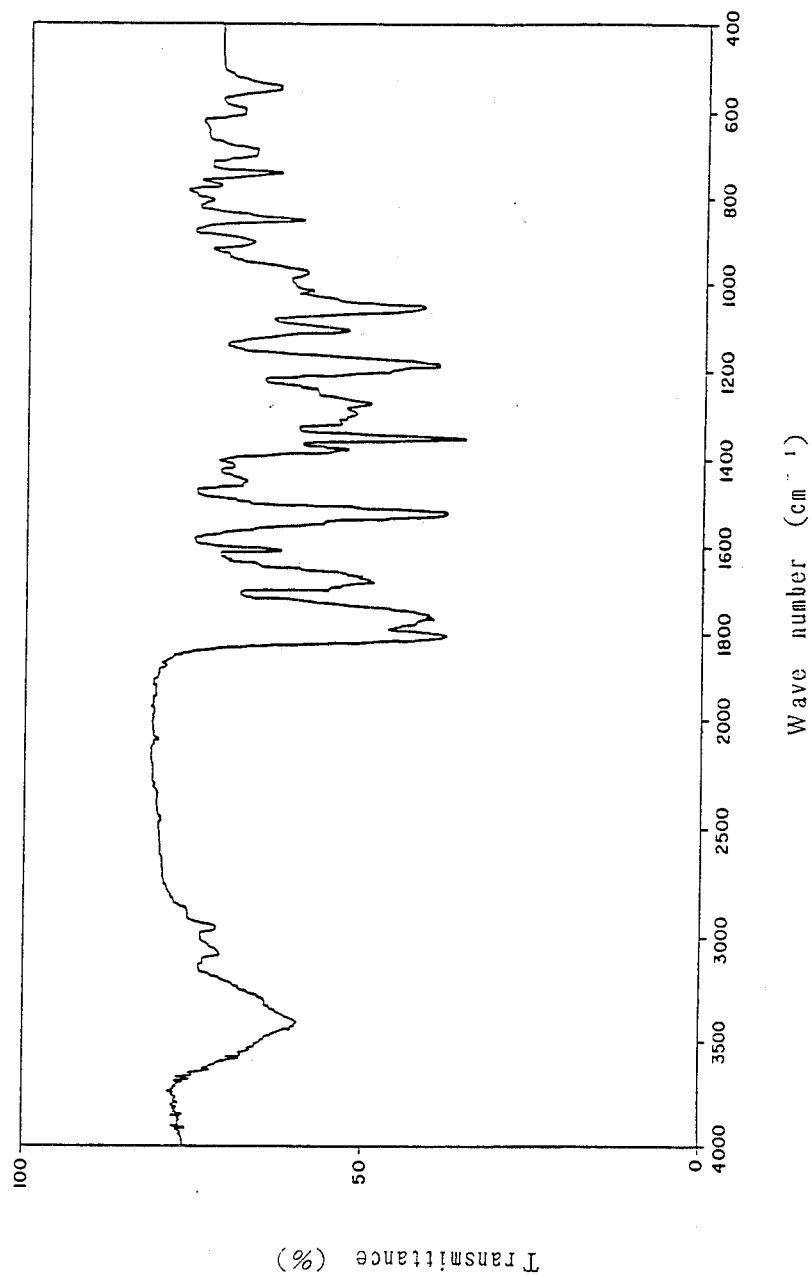
Figure 5:
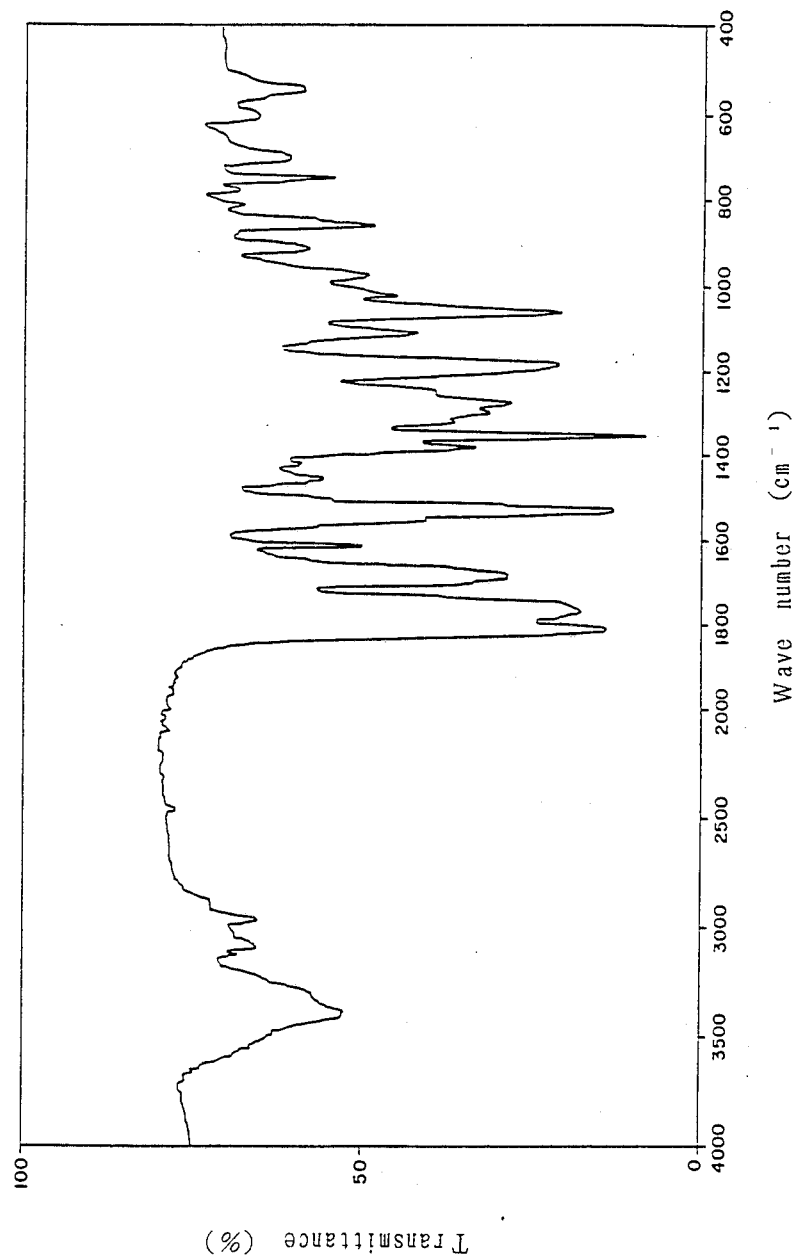
Figure 6:
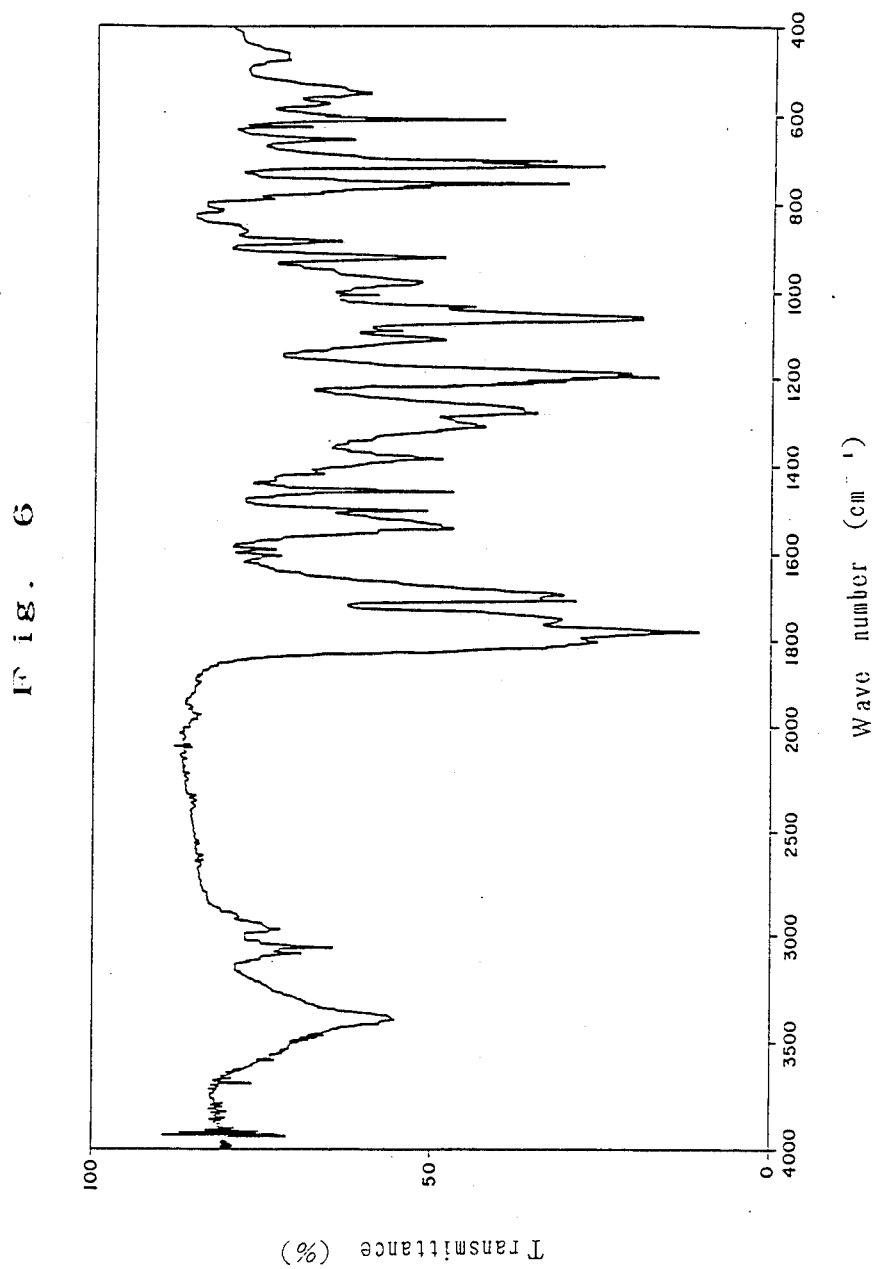
Figure 7:
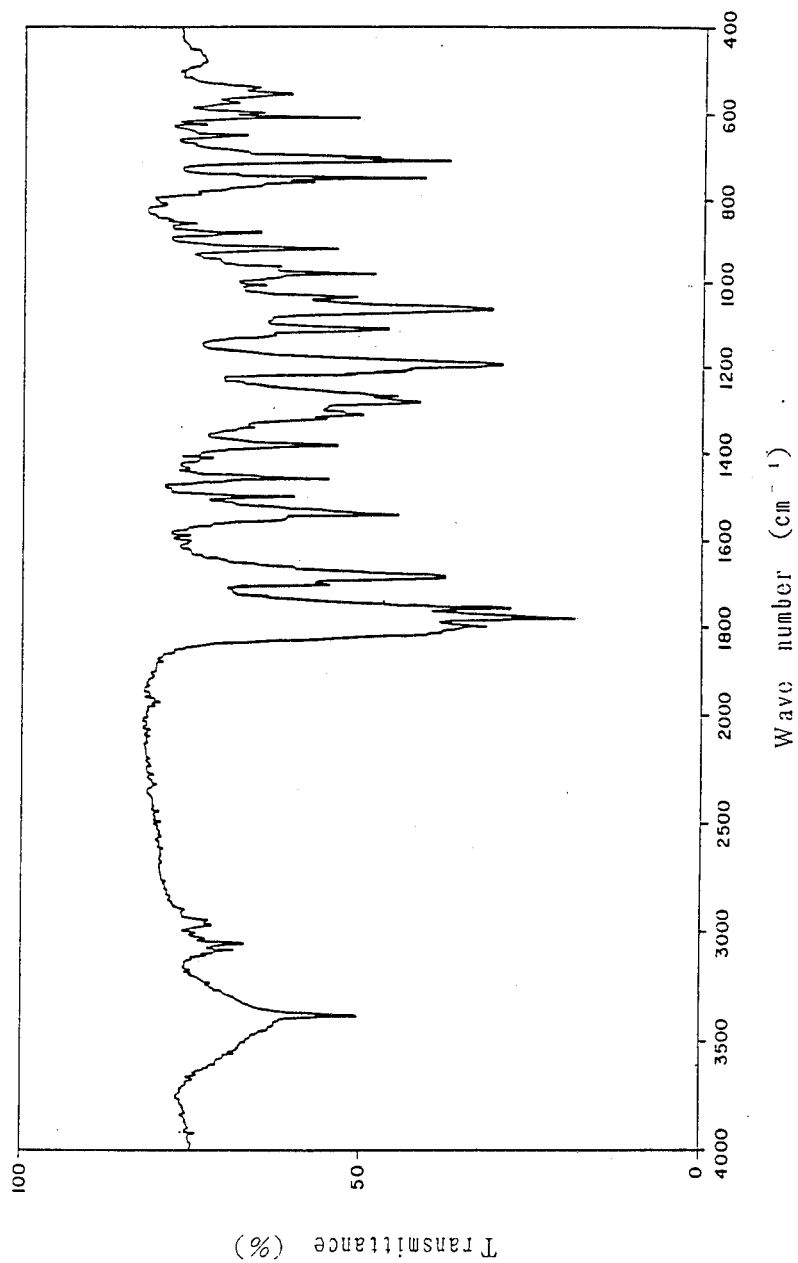
Figure 8:
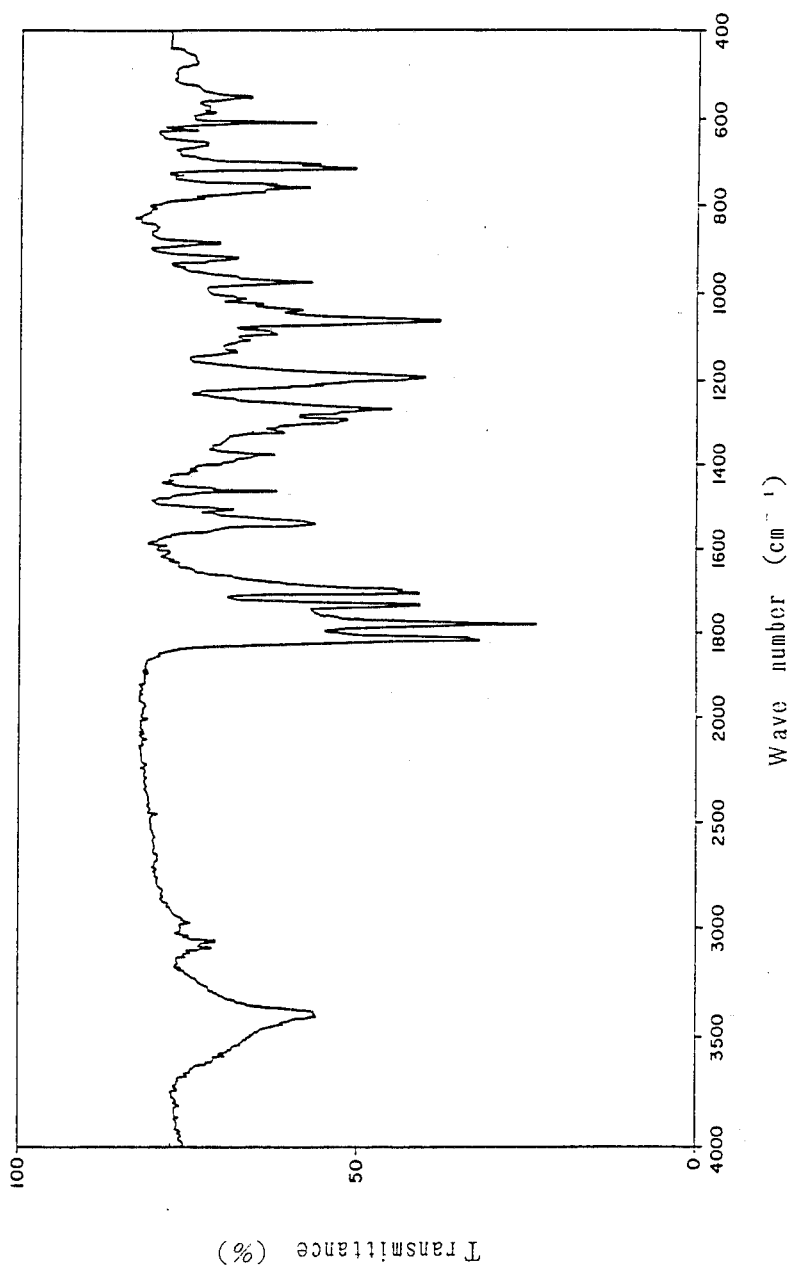
Figure 6:
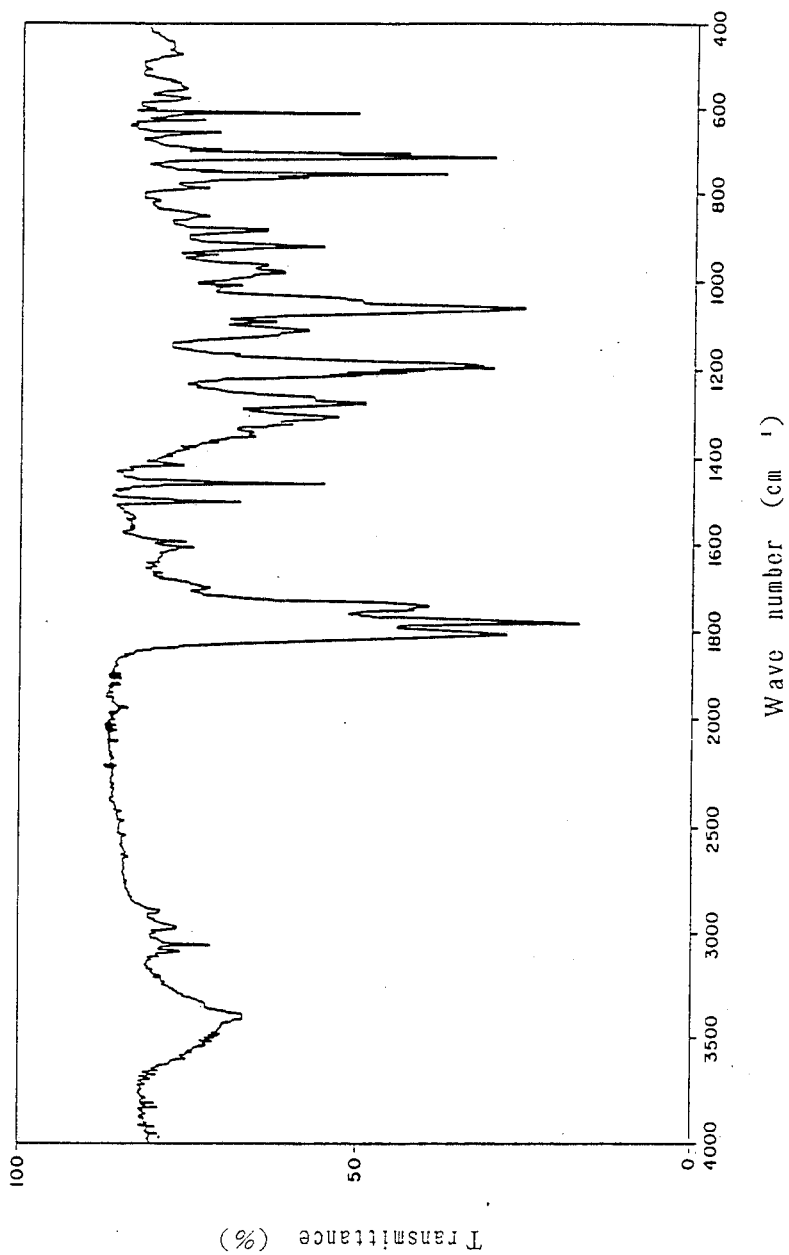
Figure 11:
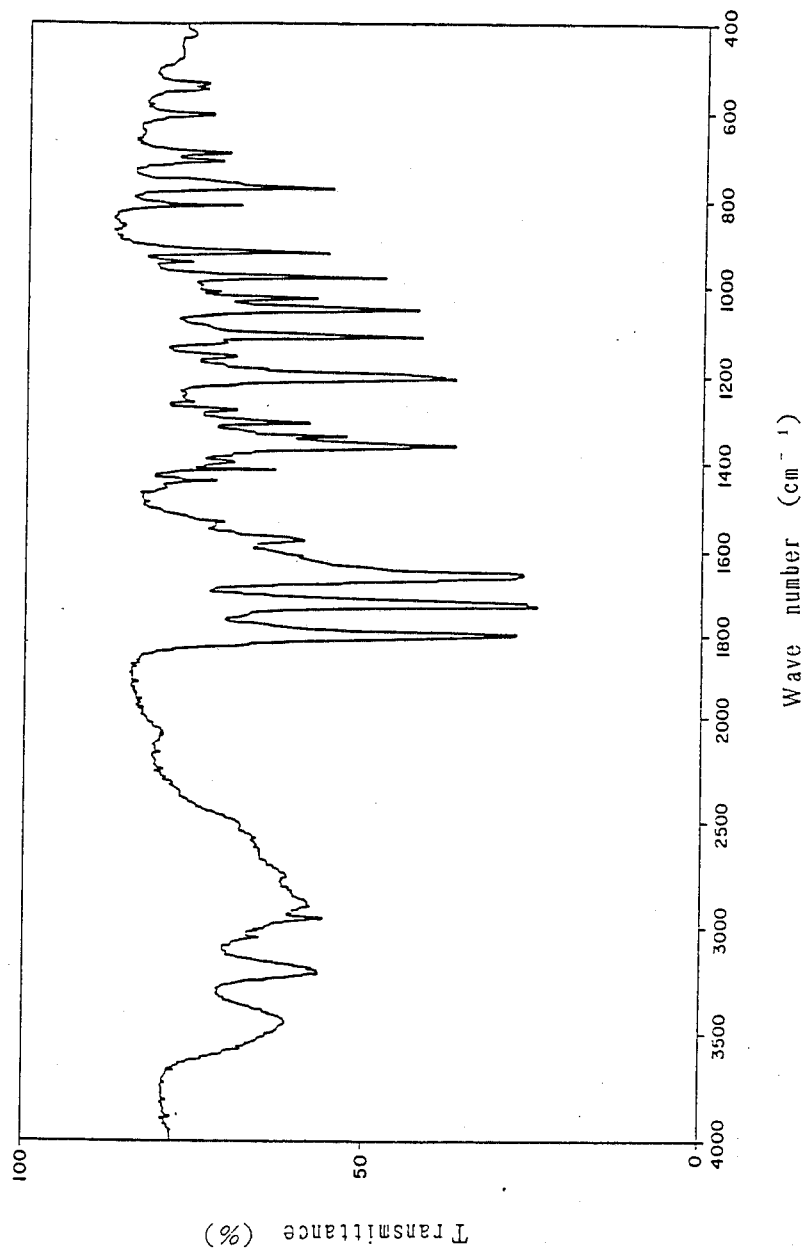
Figure 12:
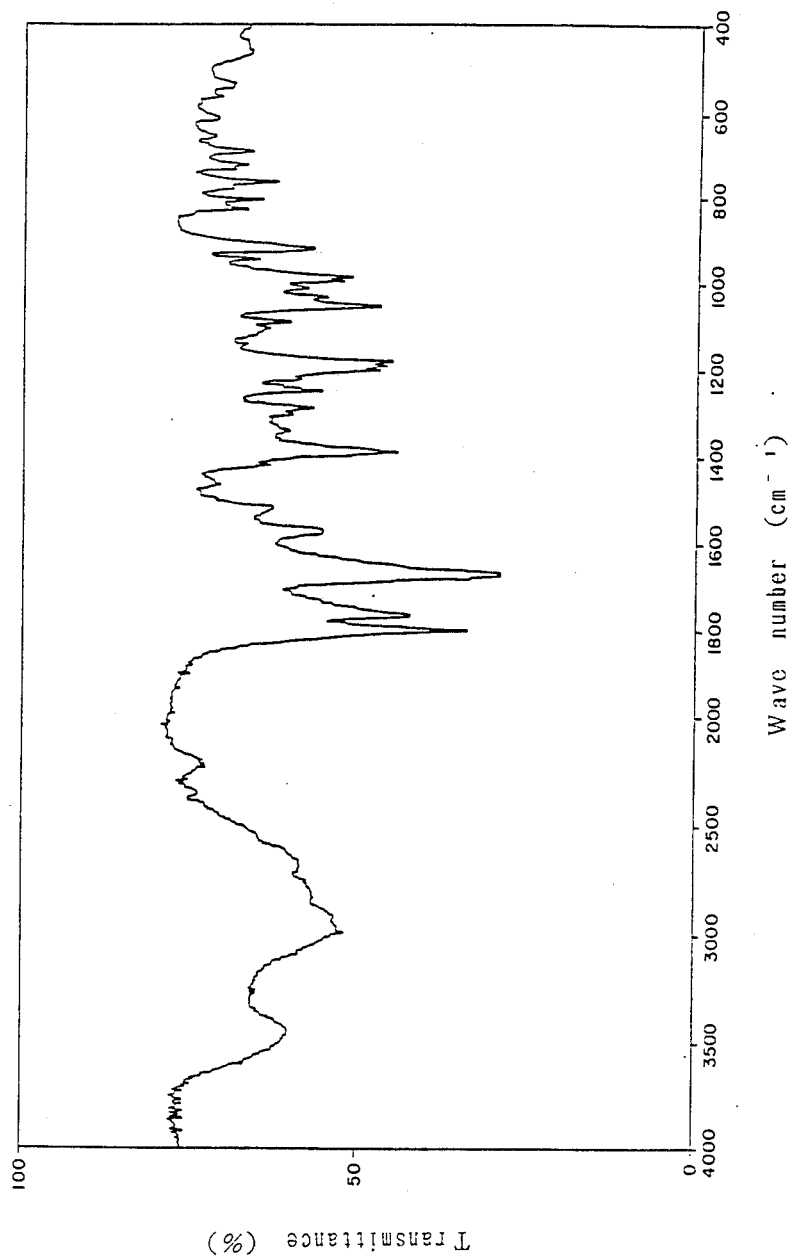

The examples and reference example are described in the following to illustrate the contents of the present invention in more particular, but it is to be understood that the present invention should not be limited by these. The term "percent" in the culture medium, unless otherwise specified, denotes "weight/volume %".

EXAMPLE 1

The strain *Empedobacter lactamqenus* YK-258 (IFO 14322, FERM BP-699) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton (produced by Daigo Nutritive Chemicals, Japan) and 0.3% of sodium chloride being supplemented with 0.5% of precipitating calcium carbonate, followed by incubation on a reciprocating shaker at 24° C. for 48 hours. The whole volume of the resulting culture broth was inoculated into a a tank of a 50-l capacity charged with 30 l of a culture medium consisting of the above culture medium being supplemented with 0.05% of Actcol (produced by Takeda Chemical Industries, Ltd., Japan), an antifoam, followed by incubation at 24° C. under the conditions of aeration at a rate of 50 l/min. and agitation at a rate of 200 r.p.m. for 48 hours. 6 l of the resulting culture broth was inoculated into a tank of a 200-l capacity charged with 120 l of a culture medium which comprises an aqueous solution (pH 6.5) containing3% of dextrin, 1.5% of raw soybean flour, 1.5% of corn gluten meal, 0.2% of Polypepton and 0.1% of sodium thiosulfate being supplemented with 0.05% of Actcol, followed by incubation at 17° C. under the conditions of aeration at a rate of 200 l/min and agitation at a rate of 150 r.p.m. for 66 hours.

After repeating the said cultivation procedure twice, the culture broth (230 l) was adjusted to pH 8, and filtered by the use of 9 kg of Hyflo Super Cel (produced by Johns Manville Co., U.S.A.). The filtrate (200 l) was adjusted to pH 6 and chromatographed on a column of Amberlite IRA-402 (Cl type, 10 l, produced by Rohm & Haas Co., U.S.A.). The antibiotic was eluted with 2% aqueous sodium chloride solution, and the eluate (53 l) was then adjusted to pH 6 and chromatographed on a column of activated carbon (5 l, produced by Takeda Chemical Industries, Ltd., Japan). The antibiotic was eluted with 8% isobutanol, and the eluate (14 l) was concentrated to 5 l under reduced pressure. The concentrate was adjusted to pH 6, and extracted with 2% tri-n-octylmethylammonium chloride/methylene chloride solution (2.5 l×2). The extract was treated with 1.6% aqueous sodium iodide solution (2.5 l) to conduct phase-transfer of the antibiotic into the water layer. The water layer was concentrated, and the concentrate was chromatographed on a column of activated carbon (500 ml), followed by eltuion with 8% isobutanol. The elute was concentrated, and the concentrate was lyophilized to give 1.41 g of a crude powder. The crude powder (14 g) was dissolved in water (100 ml), and the solution are chromatographed on a column of 200 ml of QAE-Sephadex A-25 (Cl type, produced by Pharmacia Co., Sweden), followed by elution for fractionation with 0.03M aqueous sodium chloride solution. The fractions were collected (600 ml), adjusted to pH 5.1 and desalted by chromatography on activated carbon. The eluate was concentrated and the concentrate was lyophilized to give a powder (384 mg). The powder was dissolved in water, and the solution was subjected to the preparative HPLC with use as a support of YMC-Pack SH-343 (produced by Yamamura Chemical Laboratories, Japan), followed by elution with 0.01M phosphate buffer (pH 6.3). The eluates containing the antibiotic were collected and desalted by chromatography on activated carbon, and the eluate was concentrated and lyophilized to give a white powder (141 mg) of the TAN-588 sodium salt.

EXAMPLE 2

The strain *Empedobacter lactamgenus* YK-258 (IFO 14322, FERM BP-699) grown on a nutrient agar medium was inoculated into two Sakaguchi flasks of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate, followed by incubation on a reciprocating shaker at 24° C. for 48 hours. The whole volume of the resulting culture broths was inoculated into a tank of a 200-l capacity charged with 120 l of a culture medium consisting of the above culture medium being supplemented with 0.05% of Actcol, an atifoam, followed by incubation at 24° C. under the conditions of aeration at a rate of 200 l/min and agitation at a rate of 150 r.p.m. for 48 hours. 60 l of the resulting culture broth was inoculated into a tank of a 2000-l capacity charged with 1200 l of a culture medium which consisted of an aqueous solution (pH 6.5) containing 3% of dextrin, 1.5% of raw soybean flour, 1.5% of corn gluten meal, 0.2% of Polypepton and 0.1% of sodium thiosulfate being supplemented with 0.05% of Actcol, followed by incubation at 17° C. under the conditions of aeration at a rate of 2000 l/min and agitation at a rate of 120 r.p.m. for 90 hours.

The resulting culture broth was filtered by use of Hyflo Super Cel. The filtrate (1150 l) was chromatographed on a column of 40 l of Amberlite IRA-402 (Cl type). The antibiotic was eluted with 2% aqueous sodium chloride solution (200 l), and the eluate was chromatographed on a column of activated carbon (20 l). The eluate of 8% isobutanol solution (81 l) was chromatographed on a column of 10 l of Amberlite IRA-68 (Cl type), followed by eltuion with 1% aqueous sodium chloride solution. The eluate (54 l) was again chromatographed on a column of activated carbon (10 l), and the antibiotic was eluted with 8% aqueous isobutanol. The eluate (80 l) was concentrated under reduced pressure, and the concentrate (5 l) was adjusted to pH 4.5 and extracted with 2% tri-n-octylmethylammonium chloride/methylene chloride solution (2.5 l×2). The extract was treated with 1.6% aqueous sodium iodide solution to conduct phase-transfer of the antibiotic into the water layer, and the water layer was concentrated. The concentrate (1.5 l) was subjected to a desalting procedure by means of chromatography on activated carbon (0.5 l), and the eluate was concentrated. The concentrate was chromatographed on a column of 200 ml of QAE-Sephadex (Cl type), followed by elution for fractionation with 0.03M aqueous sodium chloride solution to give an active fraction (1.3 l). The active fraction was subjected to a desalting procedure by means of chromatography on activated carbon (500 ml), and the eluate was concentrated, followed by lyophilization to give a white powder (3.56 g) of TAN-588. Since the extraction waste water layer was found to contain about 50% of the antibiotic remained, the water layer (5 l) was chromatographed on a column of 1 l of QAE-Sephadex (Cl type). The antibiotic was eluted with 0.03M and 0.05M aqueous sodium chloride solutions, and the eluate was chromatographed on a column of activated carbon (2 l). The sodium-chloride removal solution (2 l) was again extracted (1 l×2) with 2% tri-n-octylmethylammonium chloride/methylene chloride solution. The extract was treated with aqueous sodium iodide solution, followed by subjecting to a desalting step with activated carbon to give a white powder (3.18 g) of the TAN-588 sodium salt.

EXAMPLE 3

The strain *Lysobacter albus* sp. nov. YK-422 (IFO 14384, FERM BP-698) grown on a nutrient agar was inoculated into a Sakaguchi flask of a 2-l capacity charged with 500 ml of a culture medium (without pH adjustment) containing 2% of glucose, 3% of soluble starch, 1% of raw soybean flour and 0.5% of Polypepton, followed by incubation on a reciprocating shaker at 24° C. for 48 hours. The whole volume of the resulting culture broth was inoculated into a tank of a 200-l capacity charged with 120 l of a culture medium which comprises the above culture medium being supplemented with 0.05% of Actcol, an antifoam, followed by incubation at 28° C. under the conditions of aeration at a rate of 120 l/min and agitation at a rate of 180 r.p.m. for 48 hours. 120 l of the resulting culture broth was inoculated into a tank of a 6000-l capacity charged with 4000 l of a culture medium which comprises an aqueous solution (without pH adjustment) containing 3% of dextrin, 3% of raw soybean flour and 0.2% of Polypepton being supplemented with 0.05% of Actcol, followed by incubation at 22° C. under the conditions aeration at a rate of 4000 l/min and agitation at a rate of 120 r.pm. for 66 hours.

The thus-obtained culture broth was filtered by use of Hyflo Super Cel. The filtrate (4360 l) was chromatographed on a column of 400 l of Amberlite IRA-402 (Cl type). The antibiotic was eluted with 2% aqueous sodium chloride solution (2000 l), and the eluate was chromatographed on a column of activated carbon (160 l). The 8% isobutanol solution eluate (640 l) was chormatographed on a column of 40 l of Amberlite IRA-68 (Cl type), followed by elution with 1% aqueous sodium chloride solution. The eluate (200 l) was again chromatographed on a column of activated carbon (80 l), and the antibiotic was eluted with 8% aqueous isobutanol solution. The eluate (400 l) was concentrated under reduced pressure, and the concentrate was lyophilized. The lyophilized product was treated with acetone to yield the sodium salt (620 g) of TAN-588 as a precipitate. The HPLC analysis showed that the powder contained 57% of the sodium salt of TAN-588. The powder (5 g) thus obtained was dissolved in water, and the solution was chromatographed on a column of 200 ml of QAE-Sephadex (Cl type), followed by elution for fractionation with 0.03M aqueous sodium chloride solution to give the active fraction (1.2 l). The active fraction was subjected to a desalting procedure by means of chromatography on activated carbon (500 l), and the eluate was concentrated, followed by lyophilization of the concentrate to give a white powder (2.50 g) of TAN-588.

The Rf value of TLC, Rt value of HPLC and IR, UV, CD and NMR spectra as well as antimicrobial spectrum indicated that the purified powder of TAN-588 is identical to the sodium salt of TAN-588 as obtained in the above Example 1.

EXAMPLE 4

The sodium salt (400 mg) of TAN-588 was dissolved in DMF (4 ml), and triethylamine (100 μl) and p-nitrobenzyl bromide (800 mg) were added to the solution, followed by stirring at room temperature for 3 hours. 0.01M phosphate buffer (pH 6.3, 50 ml) was added to the reaction solution, and the mixture was extracted with two portions of ethyl acetate (50 ml). The extract was washed with water and concentrated, and the resulting oily material was converted into a powder (507 mg) with ethyl acetate-petroleum ether to give a mixture of TAN-588-A-p-nitrobenzyl ester and TAN-588-B-p-nitrobenzyl ester. The resulting powder was chromatographed on a column of Sephadex LH-20, with ethyl acetate:methanol=19:1 used as a mobile phase to give TAN-588-A-p-nitrobenzyl ester (105 mg) TAN- 588-B-p-nitrobenzyl ester (67 mg) and a mixture (280 mg) of both compounds.

EXAMPLE 5

In 500 ml of $CH_2Cl_2$ were dissolved 58.8 g of benzophenone hydrazone, 42 ml of 1,1,3,3-tetramethylguanidine and 150 mg of iodine, and after the mixed solution was cooled to 0° C. to −5° C., 74 g of m-chloroperbenzoic acid (with a purity of 70%) was added, followed by stirring at 0° C. for 40 minutes. The reaction solution was washed with water and dehydrated over sodium sulfate, and the solvent was distilled off to give diphenyldiazomethane.

31 g of TAN-588 was suspended in THF, and a solution of the whole diphenyldiazomethane as obtained in the above in 150 ml of THF was added to the suspension. After the mixed solution was cooled to 0° C., 60 ml of 2N HCl was added dropwise to the solution, followed by stirring at room temperature for 1 hour. 10 ml of 2N HCl was added to the reaction solution, and stirring was effected for another 1 hour, followed by addition of 3 l of $CH_2Cl_2$. The resulting solution was washed with water and concentrated, and ether was added to the residue to give 28 g of a white crystalline powder of TAN-588 benzhydryl ester (a mixture of the A type and B type).

The above mixture (1.8 g) was chromatographed on a column of silica gel (180 ml), and elution was carried out with a solvent system of chloroform:methanol (97:3), whereby the B type compound was first eluted, with the A type compound being then eluted. Each of the fractions was concentrated to give the A type compound (433 mg) and B type compound (400 mg) of TAN-588 benzhydryl ester and a mixture (476 mg) of the A type and B type compounds in the forms of colorless crystals.

EXAMPLE 6

In 1.2 l of $CH_2Cl_2$ was suspended 26 g (59 mmole) of TAN-588 benzhydryl ester (a mixture of the A type and B type) and the suspension was cooled to −20° C. 49 ml of pyridine and 37.6 g of phosphorus pentachloride were added to the suspension, followed by stirring at −10° to −15° C. for 50 minutes. After the temperature was lowered to −30° C., 180 ml of MeOH was added to the mixture, followed by stirring at −5° to −15° C. for 30 minutes and at room temperature for 1 hour. After the addition of 300 ml of 1N HCl, stirring was effected at room temperature for 45 minutes, and 100 ml of of 50% sodium phosphate and 2N NaOH (ca. 500 ml) were added to the reaction solution to adjust the pH of the aqueous layer to 8.0. The mixed solution was separated into the $CH_2Cl_2$ layer and the aqueous layer, and the aqueous layer was further extracted with $CH_2Cl_2$ (600 ml). The $CH_2Cl_2$ layers were combined and concentrated, and ether was added to the residue to give 17.9 g of a powder of benzhydryl ester (a mixture of the A type and B type) of N-deacetyl TAN-588.

EXAMPLE 7

In 10 ml of $CH_2Cl_2$ was suspended 396 mg of benzhydryl ester (a mixture of the A type and B type) of N-deacetyl TAN-588, and the suspension was cooled to −20° C., followed by addition of 434 μl of anisole and 924 μl of trifluoroacetic acid and stirring at −20° to −10° C. for 40 minutes. 280 ml of $CH_2Cl_2$ was added to reaction solution, followed by extraction with 0.1M $H_3PO_4$-$Na_2HPO_4$ solution (pH 7.3) (420 ml). The extract was adjusted to pH 5.5, and concentrated, and the concentrate was passed through a column of packed with Diaion HP-20 (50 to 100 mesh, 100 ml), followed by washing with water and elution for fractionation with 40% aqueous MeOH. The fractions exhibiting antimicrobial activity were collected and concentrated, and the concentrate was lyophilized to give 143 mg of a white powder of N-deacetyl TAN-588 (a mixture of the A type and B type).

EXAMPLE 8

In water was dissolved 100 mg of a white powder of N-deacetyl TAN-588 ( a mixture of the A type and B type), and colorless crystals separated out, upon standing at 7° C. overnight. The crystals which separated out were recovered by filtration to give 40 mg of N-deacetyl TAN-588 (the A type).

EXAMPLE 9

A 657 mg of TAN-588 benzhydryl ester (B type) was subjected to the same reaction and treatment as described in Example 6 to give 200 mg of benzhydryl ester (B type) of N-deacetyl TAN-588. 180 mg of the said compound was dissolved in 18 ml of THF:water (1:1), and 90 mg of 10% palladium-carbon was added to the solution, followed by stirring under a stream of hydrogen. After the reaction solution was filtered, the filtrate was concentrated, and the aqueous layer was washed with diethyl ether, concentrated and lyophilized to give 77 mg of a powder of N-deacetyl TAN-588 (B type).

EXAMPLE 10

The strain *Empedobacter lactamgenus* YK-258 (IFO 14322, FERM BP-699) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate, followed by incubation on a reciprocating shaker at 24° C. for 48 hours. The whole volume of the resulting culture broth was inoculated into a tank of a 50-l capacity charged with 30 l of a culture medium comprising the above culture medium being supplemented with 0.05% of Actcol, an antifoam, followed by incubation at 24° C. under the conditions of aeration at a rate of 50 l/min. and agitation at a rate of 200 r.p.m. for 48 hours. 6 l of the resulting culture broth was inoculated into a tank of a 200-l capacity charged with 120 l of a culture medium which comprises an aqueous solution (pH 6.5) containing 3% of dextrin, 1.5% of raw soybean flour, 1.5% of corn gluten meal, 0.2% of Polypepton and 0.1% of sodium thiosulfate being supplemented with 0.05% of Actcol, followed by incubation at 17° C. under the conditions of aeration at rate of 200 l/min and agitation at a rate of 150 r.p.m. for 24 hours.

It was detected by means of TLC-bioautography method using *Pseudomonas aeruginosa* C-141 that N-deacetyl TAN-588 (a mixture of the A type and B type) was contained in the cultured broth.

EXAMPLE 11

The strain *Lysobacter albus* sp. nov. YK-422 (IFO 14384, FERM BP-698) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate, followed by incubation on a reciprocating shaker at 24° C. for 48 hours. The whole volume of the resulting culture broth was inoculated into a tank of a 50-l capacity charged with 30 l of a culture medium comprising the above culture medium being supplemented with 0.05% of Actcol, an antifoam, followed by incubation at 24° C. under the conditions of aeration at a rate of 50 l/min. and agitation at a rate of 200 r.p.m. for 48 hours. 6 l of the resulting culture broth was inoculated into a tank of a 200-l capacity charged with 120 l of a culture medium which comprises an aqueous solution (pH 6.5) containing 3% of dextrin, 1.5% of raw soybean flour, 1.5% of corn gluten meal, 0.2% of Polypepton and 0.1% of sodium thiosulfate being supplemented with 0.05% of Actcol, followed by incubation at 17° C. under the conditions of aeration at a rate of 200 l/min and agitation at a rate of 150 r.p.m. for 24 hours.

It was detected by means of TLC-bioautography method using *Pseudomonas aeruginosa* C-141 that N-deacetyl TAN-588 (a mixture of the A type and B type) was contained in the culture broth.

EXAMPLE 12

The strain *Empedobacter lactamagenus* YK-258 (IFO 14322, FERM BP-699) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate, followed by incubation on a reciprocating shaker at 24° C. for 48 hours. The whole volume of the resulting culture broth was inoculated into a tank of a 50-l capacity charged with 30 l of a culture medium comprising the above culture medium being supplemented with 0.05% of Actcol, an antifoam, followed by incubation at 24° C. under the conditions of aeration at a rate of 50 l/min. and agitation at a rate of 200 r.p.m. for 48 hours.

The strain Acinetobacter sp. YK-504 (IFO 14420, FERM BP-709) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate followed by incubation on a reciprocating shaker at 24° C. for 48 hours. The whole volume of the resulting culture broth was inoculated into a tank of a 50-l capacity charged with 30 l of a culture medium comprising the above culture medium being supplemented with 0.05% of Actcol, an antifoam, followed by incubation at 24° C. under the conditions of aeration at a rate of 50 l/min. and agitation at a rate of 200 r.p.m. for 48 hours.

Three liters of said culture broth of *Empedobacter lactamgenus* YK-258 and three liters of said culture broth of Acinetobacter sp. YK-504 were inoculated into a tank of a 200-l capacity charged with 120 l of a culture medium which comprises an aqueous solution (pH 6.5) containing 3% of dextrin, 1.5% of raw soybean flour, 1.5% of corn gluten meal, 0.2% of Polypepton and 0.1% of sodium thiosulfate being supplemented with 0.05% of Actcol, followed by incubation at 24° C. under the conditions of aeration at a rate of 200 l/min and agitation at a rate of 150 r.p.m. for 24 hours, and furthermore, the cultivation was continued at 20° C. for 42 hours.

To the culture broth thus obtained is added Hyflo Super Cel, and filtration was carried out, to give 100 l of filtrate. The filtrate was adjusted to pH 5 and chromatographed on a column of Amberlite IRA-402 (Cl⁻ type, 10 l). After washing the column, elution was carried out with 2% NaCl aqueous solution (50 l). In the eluate, TAN-588 was contained at a concentration of 32 μg/ml. The effluent containing N-deacetyl TAN-588 was subjected to column chromatography of Dowex 50W X 2 (H⁺ type, 10 l) to adsorb N-deacetyl TAN-588. The eluates (50 l) with water and 0.2 N aqueous ammonia was concentrated and the concentrate (13 l) was charged to column chromatography of activated carbon (2 l) at pH 5.

The eluate (20 l) of 8% isobutanol was concentrated, and the concentrated solution (1 l) was subjected again to column chromatography of Dowex 50W X 2 (H type, 50 to 100 mesh, 0.4 l) with the elution of 0.2 N aqueous ammonia. The active fractions (1.4 l) was desalted by activated carbon column chromatography. The eluate was concentrated, and to the concentrate was added acetone, whereby crude powder was obtained.

This crude powder was subjected to the preparative HPLC with the use as a support of YMC-Pack, ODS, SH-343 [produced by Yamamura Chemical Laboratories, Japan, mobile phase: 0.02 M phosphate buffer (pH 6.3)]. The eluates containing active substance were collected, and the inorganic salt in the eluate was removed by chromatography on activated carbon. The eluates containing the antibiotic were concentrated and lyophilized, and to the lyophilizate was added acetone, whereby powders (50 mg) of N-deacetyl TAN-588 was obtained.

This powder was identified with the standard sample of N-deacetyl TAN-588 (a mixture of the A type and B type) by TLC-bioautogram, HPLC-biohistogram, IR and PMR spectra.

EXAMPLE 13

The strain *Lysobacter albus* sp. nov. YK-422 (IFO 14384, FERM BP-698) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate, followed by incubation on a reciprocating shaker at 24° C. for 48 hours. The whole volume of the resulting culture broth was inoculated into a tank of a 50-l capacity charged with 30 l of a culture medium consisting of the above culture medium being supplemented with 0.05% of Actcol, an antiform, followed by incubation at 24° C. under the conditions of aeration at a rate of 50 l/min. and agitation at a rate of 200 r.p.m. for 48 hours.

The strain Acinetobacter sp. YK-504 (IFO 14420, FERM BP-709) grown on a nutrient agar slant was inoculated into a Sakaguchi flask of a 2-l capacity charged with 500 ml of a culture medium which comprises an aqueous solution (pH 7.0) containing 2% of glucose, 3% of soluble starch, 1% of raw soybean flour, 0.5% of Polypepton and 0.3% of sodium chloride being supplemented with 0.5% of precipitating calcium carbonate, followed by incubation on a reciprocating shaker at 24° C. for 48 hours. The whole volume of the resulting culture broth was inoculated into a tank of a 50-l capacity charged with 30 l of a culture medium comprising the above culture medium being supplemented with 0.05% of Actcol, an antifoam, followed by incubation at 24° C. under the conditions of aeration at a rate of 50 l/min. and agitation at a rate of 200 r.p.m. for 48 hours.

Three liters of said culture broth of Lysobacter albus sp. nov. YK-422 and three liters of said culture broth of Acinetobacter sp. YK-504 were inoculated into a tank of a 200-l capacity charged with 120 l of a culture medium which comprises an aqueous solution (pH 6.5) containing 3% of dextrin, 1.5% of raw soybean flour, 1.5% of corn gluten meal, 0.2% of Polypepton and 0.1% of sodium thiosulfate being supplemented with 0.05% of Actcol, followed by incubation at 24° C. under the conditions of aeration at a rate of 200 l/min and agitation at a rate of 150 r.p.m. for 24 hours, and furthermore, the cultivation was continued at 20° C. for 42 hours.

It was detected by means of TLC-bioautography method using Pseudomonas aeruginosa C-141 that N-deacetyl TAN-588 (a mixture of the A type and B type) was contained in the culture broth.

EXAMPLE 14

From the results of the physico-chemical properties, decomposition and spectral studies, the structures of the compounds obtained in the foregoing Examples are elucidated to be as follows:

| Compound | $R^1$ | $R^2$ |
|---|---|---|
| (1) A type compounds: | | |

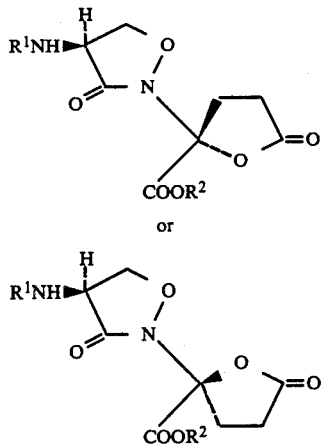

| Compound | $R^1$ | $R^2$ |
|---|---|---|
| Sodium salt of TAN-588-A | $CH_3CO-$ | Na |
| TAN-588-A-p-nitrobenzyl ester | $CH_3CO-$ | $-CH_2-\!\!\!\!\bigcirc\!\!\!\!-NO_2$ |
| TAN-588-A-benzhydryl ester | $CH_3CO-$ | $-CH(C_6H_5)_2$ |
| Benzhydryl ester of N—deacetyl TAN-588-A | H | $-CH(C_6H_5)_2$ |
| N—deacetyl TAN-588-A | H | H |

(2) B type compounds:

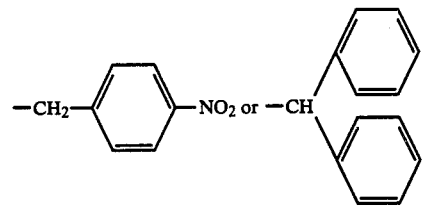

| Compound | $R^1$ | $R^2$ |
|---|---|---|
| Sodium salt of TAN-588-B | $CH_3CO-$ | Na |
| TAN-588-B-p-nitrobenzyl ester | $CH_3CO-$ | $-CH_2-\!\!\!\!\bigcirc\!\!\!\!-NO_2$ |
| TAN-588-B-benzhydryl ester | $CH_3CO-$ | $-CH(C_6H_5)_2$ |
| Benzhydryl ester of N—deacetyl TAN-588-B | H | $-CH(C_6H_5)_2$ |
| N—deacetyl TAN-588-B | H | H |

What we claim is:

1. A compound of the formula:

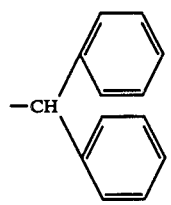

or wherein $R^1$ is H or $CH_3CO-$, $R^2$ is H, $-CH_2-\!\!\!\!\bigcirc\!\!\!\!-NO_2$ or $-CH(C_6H_5)_2$, or its salts.

2. A compound as claimed in claim 1, wherein $R^1$ is $CH_3CO-$ and $R^2$ is H.

3. A compound as claimed in claim 1, wherein $R^1$ is H and $R^2$ is $-CH(C_6H_5)_2$.

4. A compound as claimed in claim 1, wherein $R^1$ is H and $R^2$ is H.

* * * * *